United States Patent [19]

Adachi et al.

[11] Patent Number: 5,504,056
[45] Date of Patent: Apr. 2, 1996

[54] HETEROCYCLIC CYCLOHEXANEDIONE DERIVATIVE, PRODUCTION THEREOF, AND HERBICIDE

[75] Inventors: Hiroyuki Adachi, Odawara; Toshio Aihara, Hiratsuka; Katsunori Tanaka, Takaoka; Takashi Kawana, Minamiashigara; Shigeo Yamada; Hideo Hosaka, both of Odawara, all of Japan

[73] Assignee: Nippon Soda Co., Ltd., Tokyo, Japan

[21] Appl. No.: 175,420

[22] PCT Filed: Jul. 8, 1992

[86] PCT No.: PCT/JP92/00877

§ 371 Date: Jul. 20, 1994

§ 102(e) Date: Jul. 20, 1994

[87] PCT Pub. No.: WO93/01171

PCT Pub. Date: Jan. 21, 1993

[30] Foreign Application Priority Data

Jul. 9, 1991 [JP] Japan ................... 3-193594

[51] Int. Cl.$^6$ .............. C07D 211/40; C07D 211/14; A01N 43/40

[52] U.S. Cl. .............. 504/248; 546/193; 546/194; 546/242; 546/243; 549/28; 549/285; 504/244

[58] Field of Search ................. 546/193, 194, 546/242, 243; 504/248, 244

[56] References Cited

U.S. PATENT DOCUMENTS 4,761,172  8/1988  Dieter et al. ................. 504/292
4,812,160  3/1989  Dieter et al. ................. 504/292
4,921,524  5/1990  Dieter et al. ................. 504/296

*Primary Examiner*—Alan L. Rotman
*Attorney, Agent, or Firm*—Joseph C. Mason; George B. Oujevolk; Louise A. Foutch

[57] ABSTRACT

A heterocyclic cyclohexanedione derivative represented by the general formula [I]:

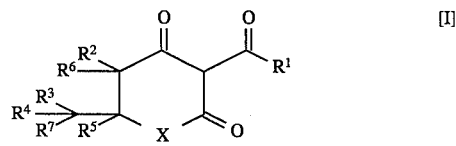

wherein $R^1$ is optionally substituted lower alkyl, optionally substituted cycloalkyl, optionally substituted phenyl or optionally substituted heterocyclic ring; $R^2$, $R^3$, $R^4$ and $R^5$ may be the same or different from one another and each independently represents hydrogen or lower alkyl; $R^6$ is hydrogen; $R^7$ is $OR^8$ wherein $R^8$ is hydrogen, lower alkyl, aralkyl, lower acyl, alkylsulfonyl or arylsulfonyl; or $R^6$ and $R^7$ are combined together to represent a single bond; X is oxygen, sulfur or N—$R^9$ wherein $R^9$ is hydrogen, lower alkyl, optionally substituted aralkyl, optionally substituted cycloalkyl, optionally substituted phenyl or optionally substituted heterocyclic ring, a salts thereof, a process for producing the same, and a herbicides comprising the same.

4 Claims, No Drawings

HETEROCYCLIC CYCLOHEXANEDIONE DERIVATIVE, PRODUCTION THEREOF, AND HERBICIDE

CROSS-REFERENCE

This application is a 35 U.S.C. §371 National Stage application of PCT/JP92/00877 filed on Jul. 8, 1992.

1. Field of the Invention

The present invention relates to a heterocyclic cyclohexanedione derivative, a process for production thereof, and a herbicide comprising the same.

2. Background of the Invention

In agricultural and horticultural crop farming, many herbicides have been used for weed control which requires extraordinary labours. However, there have been several cases which caused phytotoxicity problems and environmental pollution such as residue problems therefore, it is required to develop a new chemical entity which can provide firm effectiveness with a lower dosage and can be used safely is in a high demand.

It is an object of the present invention to provide a herbicide which can be synthesized advantageously in a industrial scale and having a property such as high effectiveness at lower dosage, highly safe, and high selectivity on crops.

DISCLOSURE OF THE INVENTION

The present invention is directed to a heterocyclic cyclohexanedione derivative represented by the general formula [I];

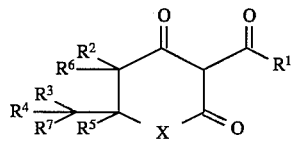

wherein $R^1$ is optionally substituted lower alkyl, optionally substituted cycloalkyl, optionally substituted phenyl or optionally substituted heterocyclic ring; $R^2$, $R^3$, $R^4$ and $R^5$ may be the same or different from one another and each represents hydrogen or lower alkyl; $R^6$ is hydrogen; $R^7$ is $OR^8$ wherein $R^8$ is hydrogen, lower alkyl, aralkyl, lower acyl, alkylsulfonyl, or arylsulfonyl; or $R^6$ and $R^7$ are combined together to represent a single bond; X is oxygen, sulfur or N—$R^9$ wherein $R^9$ is hydrogen, lower alkyl, optionally substituted aralkyl, optionally substituted cycloalkyl, optionally substituted phenyl or optionally substituted heterocyclic ring, or a salt thereof, a process for producing the same, and a herbicide comprising the same.

The substituents such as lower alkyl, cycloalkyl, phenyl and heterocyclic ring for $R^1$ may be the same or different from one another and each independently represents halogen, hydroxy, nitro, cyano, alkyl except when $R^1$ is lower alkyl, alkenyl, haloalkyl except when $R^1$ is lower alkyl, alkoxyalkyl except when $R^1$ is lower alkyl, alkoxyalkoxyalkyl except when $R^1$ is lower alkyl, alkoxycarbonylalkyl except when $R^1$ is lower alkyl, haloalkenyl, alkoxy, alkenyloxy, alkynyloxy, haloalkoxy, haloalkenyloxy, alkoxyalkoxy, alkylthioalkoxy, alkylthio, alkenylthio, alkynylthio, haloalkylthio, haloalkenylthio, monoalkylamino, dialkylamino, alkoxyakylthio, alkylthioalkylthio, alkoxycarbonyl, alkylcarbonylalkoxy, alkylcarbonyl, alkoxyamino, alkylsulfonyl, alkenylsulfonyl, alkynylsulfonyl, alkoxyalkylsulfonyl, alkylthioalkylsulfonyl, alkylsulfonylalkylsulfonyl, haloalkylsulfonyl, alkoxycarbonylalkylthio, alkylsulfinylalkoxycarbonylalkylsulfinyl, alkoxycarbonylalkylsulfonyl, alkylamide, aralkyloxy, optionally substituted phenyl, optionally substituted aralkyl, optionally substituted heterocyclic ring, or alkyl substituted by optionally substituted heterocyclic ring.

Heterocyclic ring represents pyridyl, pyrimidyl, thienyl, furyl, pirazolyl, pyrrolyl, imidazolyl, pyridazinyl, pirazinyl, indolyl, or the like.

The compounds of the present invention can be produced according to the following process.

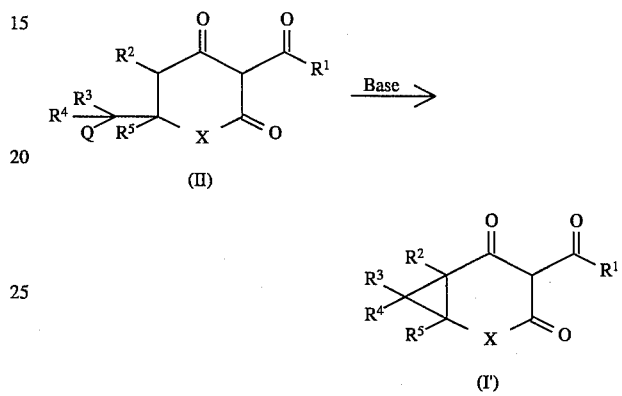

wherein $R^1$ through $R^5$ and X are as defined above, Q is a leaving group which represents halogen, alkylsulfonate, arylsulfonate, or the like.

In the process as illustrated above, compound [I'] is obtained by reacting a compound [II] in a solvent and in the presence of 2 mol or excessive concentration of a base for 30 minutes to several 10 hours at the temperature of from −20° C. to a boiling point of a solvent used, preferably from 0° C. to 50° C.

For the base described above, alkali metal hydroxides such as KOH and NaOH, alkaline earth metal hydroxides, tri($C_1$–$C_6$ alkyl)amine, pyridine, DBU, t-BuOK, triton B, sodium carbonate, sodium phosphate and the like can be used. For the solvent described above, water, alcohol, methylene chloride, benzene, toluene, ethyl acetate, dimethylformamide, THF, dimethoxyethane, acetonitrile and the like can be used by alone or in the mixture.

The compounds represented by the general formula [I] can be produced according to the following process.

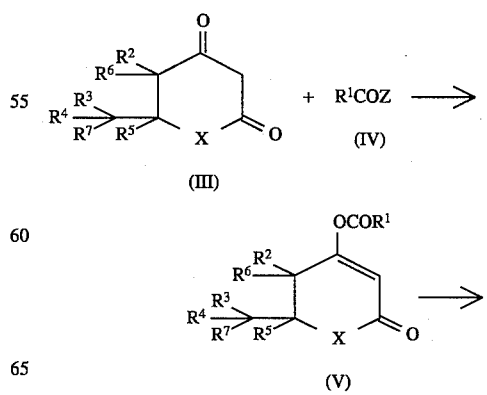

-continued

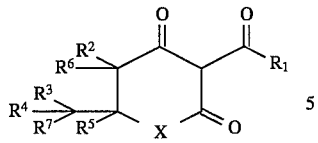

(I)

-continued

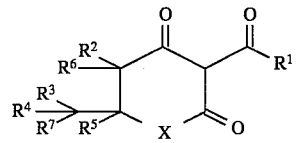

(I)

Compound [V] is obtained by reacting each 1 mol of a compound [III] and [IV], wherein Z is halogen, alkylcarbonyloxy, alkoxycarbonyloxy or benzoyloxy, in the presence of 1 mol or excessive concentration of the base.

For the base to be used, alkali metal hydroxides such as KOH and NaOH, alkaline earth metal hydroxides, tri($C_1$–$C_6$alkyl)amine, pyridine, sodium carbonate, sodium phosphate and the like can be used. For the solvent to be used, water, methylene chloride, chloroform, toluene, ethyl acetate, dimethylformamide, THF, dimethoxyethane, acetonitrile and the like can be used.

The mixture for the reaction is stirred at from 0° C. to 50° C. till the completion of the reaction. Alternatively, the mixture for the reaction can be reacted in a bilayer solvent by using a phase-transfer catalyst such as BTEAC.

Compound [V] is also obtained by reacting the compound [III] and a compound, $R^1$COOH[VI] with DCC.

For a solvent used in the reaction with DCC, methylene chloride, toluene, ethyl acetate, dimethoxyethane, acetonitrile or the like can be used. The mixture is reacted in stirring at 0° C. to 50° C. till the completion of the reaction. The mixture reacted is treated according to a customary method.

The transition reaction for the production of the compound of the present invention is carried out in the presence of a cyano compound and a mild base. For example, 1 mol of the compound [V] described above is reacted with 1 to 4 mol, preferably 2 mol of the base and 0.01 to 0.5 mol, preferably 0.05 to 0.1 mol of the cyano compound. For the base to be used in the reaction, any bases described above can be usable. For the cyano compound to be used in the reaction, polymers which retains potassium cyanide, acetonecyanohydrine, hydrogen cyanide, and potassium cyanide can be used.

By adding small amount of a phase-transfer catalyst such as crown ether, the reaction can be completed in a short time. This reaction is conducted at the temperature lower than 80° C., preferably at the range from 20° C. to 40° C. The solvents to be used can be selected among 1,2-dichloroethane, toluene, acetonitrile, methylene chloride, ethyl acetate, dimethylformamide, methylisobutylketone, THF, dimethoxyethane and the like.

The compound [I] can be obtained from the reaction of the compound [III] with the compound [VII] in the presence of a base, and a Lewis acid if necessary.

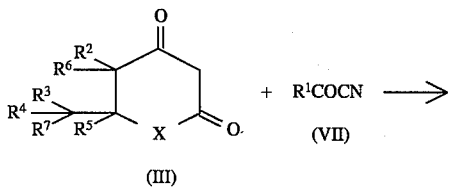

(III)          (VII)

As the base to be used in the reaction, metal hydroxides such as KOH and NaOH, alkali metal hydroxides, tri($C_1$–$C_6$ alkyl)amine, pyridine, sodium carbonate, sodium phosphate, or the like can be exemplified. For the Lewis acid suitable in this reaction, zinc chloride and ammonium trichloride can be exemplified.

The reaction is conducted at an adequate temperature in a range from –20° C. to 40° C. in an organic solvent such as acetonitrile and methylene chloride.

It is preferable to use both of zinc chloride and a base in an amount little excessive than the amount of the compound [III].

The compound represented by the general formula [II] can also led from the compound represented by the general formula [VIII].

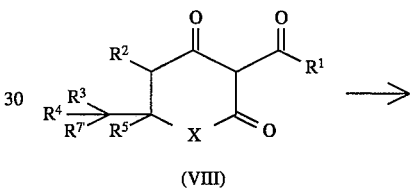

(VIII)

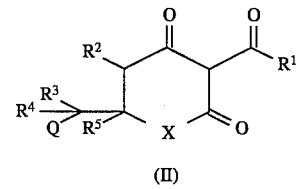

(II)

wherein $R^{7'}$ is hydroxy, lower alkoxy, aralkyloxy or acetoxy.

For example, the compound represented by the general formula [VIII] wherein $R^{7'}$ is other than OH can be produced from halogenated acid such as hydrobromic acid-acetic acid solution or by the hydrogenolysis of the compound represented by the general formula [VIII] wherein $R^{7'}$ is other than OH, and the hydrolysis thereof, if necessary. The compound represented by the general formula [II] can be obtained from the halogenation, alkylsulfonation or arylsulfonation of the compound represented by the general formula [VIII] wherein $R^{7'}$ is OH according to the commonly-known methods.

The compound represented by the general formula [III] to be used in the reaction can be synthesized according to the methods disclosed in Syn. Commun., 18, 949–963(1988); Liebigs Ann. Chem., 1975, 2261–2278; J. Heterocyclic Chem., 15, 1153–1158(1978) and Monatsh Chem., 111, 1175–1184(1980), 113, 1283–1297(1982).

The raw material compounds and the compound [I] of the present invention contain optically active substances and which can exist in forms of many tautomers as shown in the following reaction formula. All of these optically active substances and the tautomers are included in the scope of the present invention.

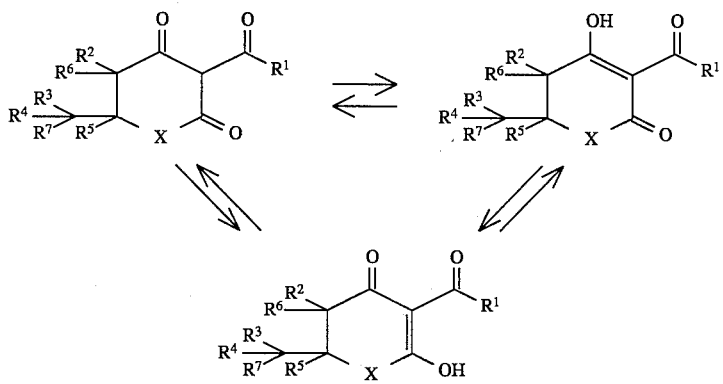

When the compound [I] contains free hydroxyl group in the reaction formula described above, the salts, particularly agriculturally and horticulturally acceptable salts, enamine or the analogs thereof, acylates, sulfonates, carbamates, or ethers can be induced from the compound [I].

For the agriculturally and horticulturally acceptable salts adequate for the above reaction formula, sodium salts, potassium salts, calcium salts and ammonium salts are exemplified.

For examples of the ammonium salts described above, the salts of $N^+R^aR^bR^cR^d$ wherein $R^a$, $R^b$, $R^c$ and $R^d$ are each independently selected from $C_1$–$C_{10}$ alkyls substituted by hydrogen, or occasionally hydroxy, can be exemplified. If any of $R^a$, $R^b$, $R^c$ and $R^d$ is alkyl occasionally substituted, the one which contains 1 to 4 carbon atoms therein are preferable.

The adequate enamines or the analogs thereof are the one of which OH portion is independently converted to —$NR^eR^f$ wherein $R^e$ is alkyl or aryl such as phenyl which contains 1 to 6 carbon atoms and is occasionally substituted; $R^f$ is hydrogen or, alkyl or aryl such as phenyl which contains 1 to 6 carbon atoms and is occasionally substituted, halogen or $SR^g$ wherein $R^g$ is the same as $R^e$ described above. An adequate acylate or ether derivative is the one of which OH portion is converted to —$OC(O)NR^iR^g$ wherein $R^i$ and $R^g$ are each independently hydrogen or the same as $R^e$ described above. These derivatives can be produced according to a customary method.

After the completion of the reaction, the objective products can be obtained through a customary post-treatment procedure. The chemical structures of the compounds of the present invention are determined according to IR, NMR, MS, etc.

BEST MODE FOR CARRYING OUT THE INVENTION

Now, the compounds according to the present invention are further explained in detail with referring to the following Examples.

EXAMPLE 1

4-(4-chloro-2-nitrobenzoyl)-2-oxabicyclo[4.1.0]heptane-3,5-dione (Compound No. I-2)

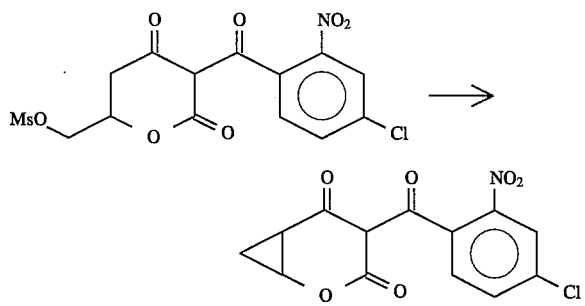

To 10 ml of ethanol was dissolved 0.95 g (2.3 mmole) of 6-mesyloxymethyl-3-(4-chloro-2-nitrobenzoyl)-tetrahydro-pyran-2,4-dione, and was further added 3.3 g (5.8 mmole) of 7% aqueous solution of sodium hydrate at room temperature, then allowed for stirring for 16 hours. After the completion of the reaction, the mixture was poured into ice water, acidified with diluted hydrochloric acid to extract it with chloroform. The organic solvent layer extracted was washed with saturated brine, dried with magnesium sulfate, then the solvent was distilled. To the residue was added methanol, then it is crystallized to obtain 0.20 g of the objective product in whitish crystals. The melting point thereof was from 137° to 139° C.

EXAMPLE 2

4-(2,3-dimethyl-4-methylsulfonylbenzoyl)-2-oxabicyclo[4.1.0]heptane-3,5-dione (compound No. I-4)

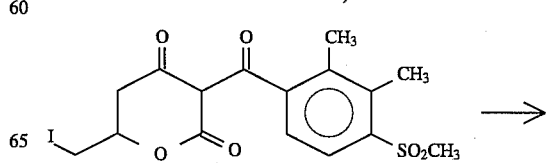

-continued

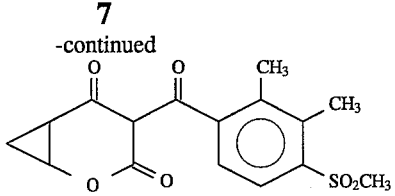

To 15 ml of benzene was dissolved 0.70 g (1.5 mmole) of 6-iodomethyl-3-(2,3-dimethyl-4-methylsulfonylbenzoyl)-tetrahydropyran-2,4-dione, and 0.57 g (3.8 mmole) of DBU was added thereto at room temperature, then stirred it for 2 days. After the completion of the reaction, distilled benzene from the solution, and the residue was added with ice water, acidified with diluted hydrochloric acid, and extracted with chloroform. The organic solvent layer extracted was washed with saturated brine, dried with magnesium sulfate, then distilled the solvent therein. The residue was purified by silica gel column chromatography (chloroform) to obtain 0.35 g of the objective product in whitish crystals. The melting point thereof was from 0° C. to 2° C.

EXAMPLE 3

4-(4-chloro-2-nitrobenzoyl)-2-methyl-2-azabicyclo[4.1.0]heptane-3,5-dione (Compound No. I-10)

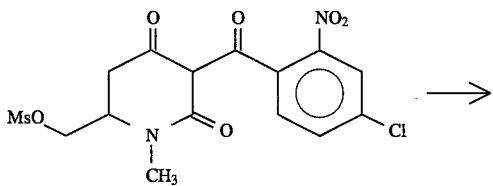

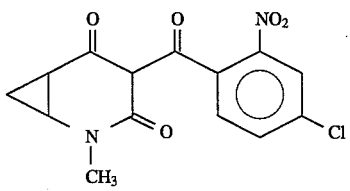

To 10 ml of ethanol was dissolved 1.30 g (3.1 mmole) of 6-mesyloxymethyl-3-(4-chloro-2-nitrobenzoyl)-1-methylpiperidine-2,4-dione, and 3.4 g (9.3 mmole) of 10% aqueous solution of sodium hydrate was added thereto at room temperature, then stirred it for 4 hours. After the completion of the reaction, the mixture was poured into ice water, acidified with diluted hydrochloric acid, and extracted with chloroform. The organic solvent layer extracted was washed with saturated brine, dried with magnesium sulfate, then distilled the solvent therein. The residue was purified by silica gel column chromatography (chloroform), then obtained 0.30 g of the objective product in pale yellowish crystals. The melting point thereof was from 145° C. to 146° C.

EXAMPLE 4

6-benzyloxymethyl-3-(4-chloro-2-nitrobenzoyl)-tetrahydropyran-2,4-dione (Compound No. II-2)

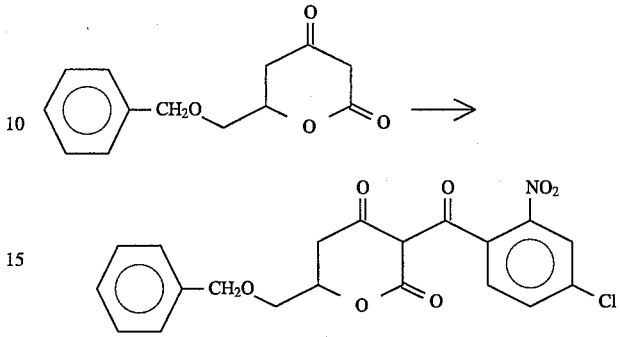

To 20 ml of methylene chloride were dissolved 2.00 g (8.6 mmole) of 6-benzyloxymethyltetrahydropyran-2,4-dione and 1.01 g (10.0 mmole) of triethylamine, and 1.88 g (8.6 mmole) of 4-chloro-2-nitrobenzoylchloride was added thereto at room temperature, then stirred the mixture for 30 minutes. The solution for the reaction was washed with diluted hydrochloric acid, water and saturated brine respectively in turn, the organic solvent layer thereof was dried with magnesium sulfate, then distilled the solvent to obtain 4.0 g of o-benzoyl compound. The o-benzoyl compound was dissolved into 30 ml of acetonitrile, added with 2.02 g (20.0 mmole) of triethylamine and 0.27 g (3.2 mmole) of acetonecyanohydrine at room temperature, and stirred the mixture for 16 hours. After the completion of the reaction, diluted hydrochloric acid was added to the resulting product, which is then extracted with chloroform. The organic solvent layer extracted was washed with saturated brine, dried with magnesium sulfate, then the solvent was distilled therefrom. The residue was purified by silica gel column chromatography (chloroform) to obtain 2.40 g of objective product in a state of sticky oil.

EXAMPLE 5

6-acetoxymethyl-3-(4-chloro-2-nitrobenzoyl)tetrahydropyran-2,4-dione (Compound No. II-3)

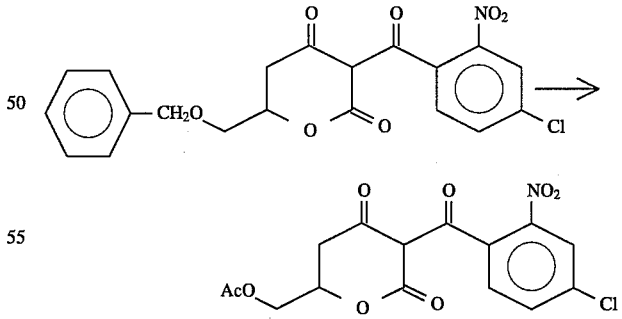

To 7.7 ml of 25% acetic acid solution of hydrobromic acid was dissolved 2.40 g (5.7 mmole) of 6-benzyloxymethyl-3-(4-chloro-2-nitrobenzoyl)tetrahydropyran-2,4-dione, then this solution was reacted at room temperature for 5 hours. After the completion of the reaction, the mixture was poured into ice water, then extracted with chloroform. The organic solvent layer extracted was washed with water and saturated brine in turn, dried with magnesium sulfate, then the solvent was distilled therefrom. The residue obtained was purified by silica gel column chromatography to obtain 1.50 g of the objective product in a state of orange-coloured sticky oil.

EXAMPLE 6

6-hydroxymethyl-3-(4-chloro-2-nitrobenzoyl)-tetrahydropyran-2,4-dione (Compound No. II-1)

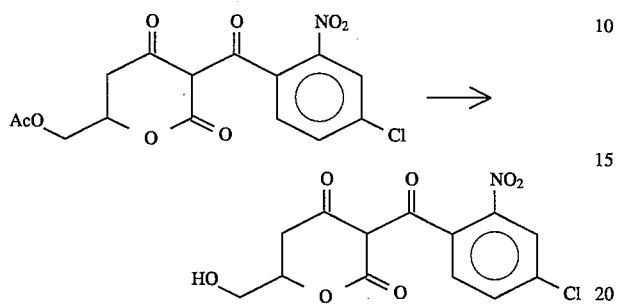

To 10 ml of ethanol was dissolved 1.50 g (4.1 mmole) of 6-acetoxymethyl-3-(4-chloro-2-nitrobenzoyl)-tetrahydropyran-2,4-dione, then 8.0 ml of 1N aqueous solution of sodium hydroxide was added thereto to react for 1 hour at room temperature. The solution for the reaction was poured into ice water, acidified with diluted hydrochloric acid, then extracted with chloroform. The organic solvent layer extracted was washed with water and saturated brine in turn, dried with magnesium sulfate, and the solvent therein was distilled. The resulting crystals were washed with methanol, then 0.90 g of the objective product was obtained in whitish crystals. The melting point thereof was from 135° to 137° C.

EXAMPLE 7

6-mesyloxymethyl-3-(4-chloro-2-nitrobenzoyl)-tetrahydropyran-2,4-dione (Compound No. II-4)

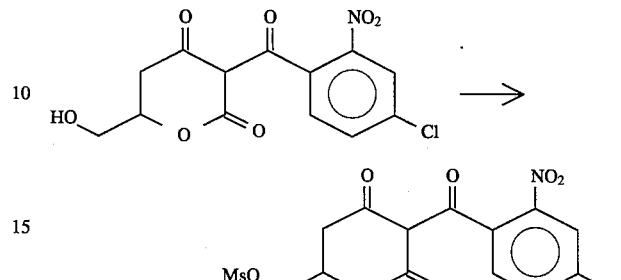

To 20 ml of methylene chloride was dissolved 1.27 g (3.9 mmole) of 6-hydroxymethyl-3-(4-chloro-2-nitrobenzoyl)-tetrahydropyran-2,4-dione and 1.20 g (11.6 mmole) of triethylamine, then 1.00 g (5.8 mmole) of methanesulfonate anhydride was added thereto, then the mixture was reacted for 2 hour at room temperature. After the completion of the reaction, the reacted product was poured into ice water, acidified with diluted hydrochloric acid, then the organic solvent layer thereof was washed with water and saturated brine in turn, dried with magnesiun sulfate. The solvent therein was distilled to obtain 1.55 g of the objective product in whitish crystals. The representative examples including the products obtained in the examples described above are shown in Tables 1 through 4.

TABLE 1

Stuctural formula

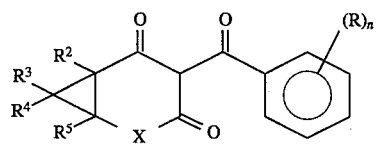

| Compound No. | (R)ₙ | R² | R³ | R⁴ | R⁵ | X | Physical constant [ ] m.p. °C. |
|---|---|---|---|---|---|---|---|
| I-1 | 4-Cl-2-NO₂ | H | H | H | CH₃ | O | [150–151] |
| I-2 | " | " | " | " | H | " | [137–139] |
| I-3 | 4-SO₂CH₃-2-NO₂ | " | " | " | " | " | [198–199] decomposed |
| I-4 | 2,3-(CH₃)₂-4-SO₂CH₃ | " | " | " | " | " | [170–172] |
| I-5 | 2-Cl-3-OCH₃-4-SO₂CH₃ | " | " | " | " | " | powder*¹ |
| I-6 | 2-CH₃-3-OCH₃-4-SO₂CH₃ | " | " | " | " | " | |
| I-7 | 2-Cl-3-CO₂CH₃-4-SO₂CH₃ | " | " | " | " | " | |
| I-8 | 2-Cl-4-SO₂CH₃ | " | " | " | " | " | |
| I-9 | 2-NO₂-4-CF₃ | " | " | " | " | " | |
| I-10 | 2-NO₂-4-Cl | " | " | " | " | NCH₃ | [145–146] |
| I-11 | 2-NO₂-4-Cl | H | H | H | H | NH | |
| I-12 | " | " | " | " | " | NC₂H₅ | [98–9] |
| I-13 | " | " | " | " | " | NC₃H₇ⁱ | |
| I-14 | " | " | " | " | " | N—CH₂—C₆H₄—OCH₃ | powder*² |
| I-15 | 2-NO₂ | " | " | " | " | NH | |
| I-16 | " | " | " | " | " | NCH₃ | [136–8° C.] |
| I-17 | 2-NO₂-4-CF₃ | " | " | " | " | NH | |
| I-18 | " | " | " | " | " | NCH₃ | |

TABLE 1-continued

Stuctural formula

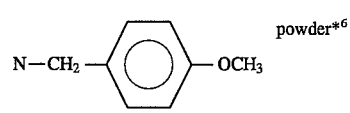

| Compound No. | (R)$_n$ | R$^2$ | R$^3$ | R$^4$ | R$^5$ | X | Physical constant [ ] m.p. °C. |
|---|---|---|---|---|---|---|---|
| I-19 | " | " | " | " | " | NC$_2$H$_5$ | |
| I-20 | 2-NO$_2$-4-SCH$_3$ | " | " | " | " | NH | |
| I-21 | " | " | " | " | " | NCH$_3$ | n$_D^{27.6}$ 1.6137 |
| I-22 | " | " | " | " | " | NC$_2$H$_5$ | |
| I-23 | 2-NO$_2$-4-SOCH$_3$ | " | " | " | " | NH | |
| I-24 | " | " | " | " | " | NCH$_3$ | |
| I-25 | 2-NO$_2$-4-SO$_2$CH$_3$ | H | H | H | H | NH | |
| I-26 | " | " | " | " | " | NCH$_3$ | powder*3 |
| I-27 | " | " | " | " | " | NC$_2$H$_5$ | |
| I-28 | 2,4-Cl$_2$ | " | " | " | " | NH | |
| I-29 | " | " | " | " | " | NCH$_3$ | |
| I-30 | 3,4-Cl$_2$ | " | " | " | " | NH | |
| I-31 | " | " | " | " | " | NCH$_3$ | [116–7] |
| I-32 | 2-Cl-4-SO$_2$CH$_3$ | " | " | " | " | NH | |
| I-33 | " | " | " | " | " | NCH$_3$ | powder*4 |
| I-34 | " | " | " | " | " | NC$_2$H$_5$ | |
| I-35 | 2,3-Cl$_2$-4-SO$_2$CH$_3$ | " | " | " | " | NH | |
| I-36 | " | " | " | " | " | NCH$_3$ | |
| I-37 | " | " | " | " | " | NC$_2$H$_5$ | |
| I-38 | " | " | " | " | " | NC$_3$H$_7^i$ | |
| I-39 | 2-Cl-3-CH$_3$-4-SO$_2$CH$_3$ | H | H | H | H | NH | |
| I-40 | " | " | " | " | " | NCH$_3$ | |
| I-41 | " | " | " | " | " | NC$_2$H$_5$ | |
| I-42 | " | " | " | " | " | NC$_3$H$_7^i$ | |
| I-43 | 2-Cl-3-CH$_2$OCH$_2$CH$_2$OCH$_3$-4-SO$_2$CH$_3$ | " | " | " | " | NH | |
| I-44 | " | " | " | " | " | NCH$_3$ | |
| I-45 | " | " | " | " | " | NC$_2$H$_5$ | |
| I-46 | " | " | " | " | " | NC$_3$H$_7^i$ | |
| I-47 | 2-Cl-3-CO$_2$CH$_3$-4-SO$_2$CH$_3$ | " | " | " | " | NH | |
| I-48 | " | " | " | " | " | NCH$_3$ | |
| I-49 | " | CH$_3$ | " | " | " | " | |
| I-50 | " | H | " | " | CH$_3$ | " | |
| I-51 | " | " | " | " | H | NC$_2$H$_5$ | |
| I-52 | " | CH$_3$ | " | " | " | " | |
| I-53 | 2-Cl-3-CO$_2$CH$_3$-4-SO$_2$CH$_3$ | H | H | H | CH$_3$ | NC$_2$H$_5$ | |
| I-54 | " | " | " | " | H | NC$_3$H$_7^i$ | |
| I-55 | 2-Cl-3-CH$_2$OCH$_3$-4-SO$_2$CH$_3$ | " | " | " | " | NH | |
| I-56 | " | " | " | " | " | NCH$_3$ | |
| I-57 | 2-Cl-3-CH$_2$CH$_2$OCH$_3$-4-SO$_2$CH$_3$ | " | " | " | " | NH | |
| I-58 | " | " | " | " | " | NCH$_3$ | |
| I-59 | 2-Cl-3-CH$_2$COOCH$_3$-4-SO$_2$CH$_3$ | " | " | " | " | NH | |
| I-60 | " | " | " | " | " | NCH$_3$ | |
| I-61 | 2-Cl-3-C$_2$H$_5$-4-SO$_2$CH$_3$ | " | " | " | " | NH | |
| I-62 | " | " | " | " | " | NCH$_3$ | |
| I-63 | 2-Cl-3-C$_3$H$_7^i$-4-SO$_2$CH$_3$ | " | " | " | " | NH | |
| I-64 | " | " | " | " | " | NCH$_3$ | |
| I-65 | 2-Cl-3-OCH$_3$-4-SO$_2$CH$_3$ | " | " | " | " | NH | powder*5 |
| I-66 | " | CH$_3$ | " | " | " | " | |
| I-67 | 2-Cl-3-OCH$_3$-4-SO$_2$CH$_3$ | H | H | H | CH$_3$ | NH | |
| I-68 | " | " | " | " | H | NCH$_3$ | [141–3] |
| I-69 | " | CH$_3$ | " | " | " | " | |
| I-70 | " | H | " | " | CH$_3$ | " | |
| I-71 | " | " | " | " | H | NC$_2$H$_5$ | [154–5] |
| I-72 | " | CH$_3$ | " | " | " | " | |
| I-73 | " | H | " | " | CH$_3$ | " | |
| I-74 | " | " | " | " | H | NC$_3$H$_7^i$ | |
| I-75 | " | CH$_3$ | " | " | " | " | |
| I-76 | " | H | " | " | CH$_3$ | " | |
| I-77 | " | " | " | " | H | N—CH$_2$—⟨phenyl⟩—OCH$_3$ | powder*6 |
| I-78 | " | CH$_3$ | " | " | " | " | |
| I-79 | 2-Cl-3-OC$_3$H$_7^i$-4-SO$_2$CH$_3$ | H | " | " | " | NH | |

TABLE 1-continued

Structural formula

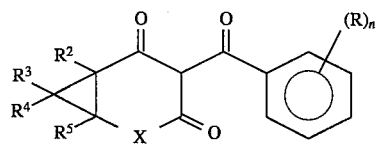

| Compound No. | (R)$_n$ | R$^2$ | R$^3$ | R$^4$ | R$^5$ | X | Physical constant [ ] m.p. °C. |
|---|---|---|---|---|---|---|---|
| I-80 | " | " | " | " | " | NCH$_3$ | |
| I-81 | 2-Cl-3-OC$_4$H$_9$$^n$-4-SO$_2$CH$_3$ | H | H | H | H | NH | |
| I-82 | " | " | " | " | " | NCH$_3$ | |
| I-83 | " | " | " | " | " | NC$_2$H$_5$ | |
| I-84 | " | " | " | " | " | NC$_3$H$_7$$^i$ | |
| I-85 | 2-Cl-3-OCH$_2$CH=CH$_2$-4-SO$_2$CH$_3$ | " | " | " | " | NH | |
| I-86 | " | CH$_3$ | " | " | " | " | |
| I-87 | " | H | " | " | " | NCH$_3$ | |
| I-88 | " | CH$_3$ | " | " | " | " | |
| I-89 | " | H | " | " | " | NC$_2$H$_5$ | |
| I-90 | " | " | " | " | " | NC$_3$H$_7$$^i$ | |
| I-91 | 2-Cl-3-OCH$_2$C≡CH-4-SO$_2$CH$_3$ | " | " | " | " | NH | |
| I-92 | " | CH$_3$ | " | " | " | " | |
| I-93 | " | H | " | " | CH$_3$ | " | |
| I-94 | " | " | " | " | H | NCH$_3$ | |
| I-95 | 2-Cl-3-OCH$_2$C≡CH-4-SO$_2$CH$_3$ | CH$_3$ | H | H | H | NCH$_3$ | |
| I-96 | " | H | " | " | CH$_3$ | " | |
| I-97 | " | " | " | " | H | NC$_2$H$_5$ | |
| I-98 | " | CH$_3$ | " | " | " | " | |
| I-99 | " | H | " | " | " | NC$_3$H$_7$$^i$ | |
| I-100 | 2-Cl-3-OCH$_2$CH=CHCl-4-SO$_2$CH$_3$ | " | " | " | " | NH | |
| I-101 | " | " | " | " | " | NCH$_3$ | |
| I-102 | 2-Cl-3-OCH$_2$CH$_2$OCH$_3$-4-SO$_2$CH$_3$ | " | " | " | " | NH | |
| I-103 | " | CH$_3$ | " | " | " | " | |
| I-104 | " | H | " | " | CH$_3$ | " | |
| I-105 | " | " | " | " | H | NCH$_3$ | powder*$^7$ |
| I-106 | " | CH$_3$ | " | " | " | " | |
| I-107 | " | H | " | " | CH$_3$ | " | |
| I-108 | " | " | " | " | H | NC$_2$H$_5$ | |
| I-109 | 2-Cl-3-OCH$_2$CH$_2$OCH$_3$-4-SO$_2$CH$_3$ | CH$_3$ | H | H | H | NC$_2$H$_5$ | |
| I-110 | " | H | " | " | CH$_3$ | " | |
| I-111 | " | " | " | " | H | NC$_3$H$_7$$^i$ | |
| I-112 | 2-Cl-3-OCH$_2$CH$_2$OC$_2$H$_5$-4-SO$_2$CH$_3$ | " | " | " | " | NH | |
| I-113 | " | " | " | " | " | NCH$_3$ | |
| I-114 | 2-Cl-3-OCH$_2$CH$_2$SCH$_3$-4-SO$_2$CH$_3$ | " | " | " | " | NH | |
| I-115 | " | " | " | " | " | NCH$_3$ | |
| I-116 | " | " | " | " | " | NC$_2$H$_5$ | |
| I-117 | " | " | " | " | " | NC$_3$H$_7$$^i$ | |
| I-118 | " | " | " | " | " | NC$_3$H$_7$ | |
| I-119 | 2-Cl-3-OCH$_2$CH$_2$CH$_2$OCH$_3$-4-SO$_2$CH$_3$ | " | " | " | " | NH | |
| I-120 | " | " | " | " | " | NCH$_3$ | |
| I-121 | " | " | " | " | " | NC$_2$H$_5$ | |
| I-122 | " | " | " | " | " | NC$_3$H$_7$$^i$ | |
| I-123 | 2-Cl-3-OCH$_2$CH(CH$_3$)—OCH$_3$-4-SO$_2$CH$_3$ | H | H | H | H | NH | |
| I-124 | " | " | " | " | " | NCH$_3$ | |
| I-125 | 2-Cl-3-SCH$_3$-4-SO$_2$CH$_3$ | " | " | " | " | NH | |
| I-126 | " | " | " | " | " | NCH$_3$ | |
| I-127 | 2,3-(CH$_3$)$_2$-4-SO$_2$CH$_3$ | " | " | " | " | NH | |
| I-128 | " | CH$_3$ | " | " | " | " | |
| I-129 | " | H | " | " | CH$_3$ | " | |
| I-130 | " | " | " | " | H | NCH$_3$ | |
| I-131 | " | CH$_3$ | " | " | " | " | |
| I-132 | " | H | " | " | CH$_3$ | " | |
| I-133 | " | " | " | " | H | NC$_2$H$_5$ | |
| I-134 | " | CH$_3$ | " | " | " | " | |
| I-135 | " | H | " | " | CH$_3$ | " | |
| I-136 | " | " | " | " | H | NC$_3$H$_7$$^i$ | |
| I-137 | 2-CH$_3$-3-Cl-4-SO$_2$CH$_3$ | H | H | H | H | NH | |
| I-138 | " | " | " | " | " | NCH$_3$ | |
| I-139 | " | " | " | " | " | NC$_2$H$_5$ | |

TABLE 1-continued

Structural formula $$\begin{array}{c} R^2 \\ R^3 \\ R^4 \\ R^5 \end{array} \diagdown X \diagdown \begin{array}{c} O \\ \| \\ C \end{array} \diagdown \begin{array}{c} O \\ \| \\ C \end{array} \diagdown \begin{array}{c} O \\ \| \\ C \end{array} \diagdown (R)_n$$

| Compound No. | (R)$_n$ | R$^2$ | R$^3$ | R$^4$ | R$^5$ | X | Physical constant [ ] m.p. °C. |
|---|---|---|---|---|---|---|---|
| I-140 | " | " | " | " | " | NC$_3$H$_7^i$ | |
| I-141 | 2-CH$_3$-3-CO$_2$CH$_3$-4-SO$_2$CH$_3$ | " | " | " | " | NH | |
| I-142 | " | " | " | " | " | NCH$_3$ | |
| I-143 | " | " | " | " | " | NC$_2$H$_5$ | |
| I-144 | " | " | " | " | " | NC$_3$H$_7^i$ | |
| I-145 | 2-CH$_3$-3-OCH$_3$-4-SO$_2$CH$_3$ | " | " | " | " | NH | |
| I-146 | " | CH$_3$ | " | " | " | " | |
| I-147 | " | H | " | " | CH$_3$ | " | |
| I-148 | " | " | " | " | H | NCH$_3$ | [144–5] |
| I-149 | " | CH$_3$ | " | " | " | " | |
| I-150 | " | H | " | " | CH$_3$ | " | |
| I-151 | 2-CH$_3$-3-OCH$_3$-4-SO$_2$CH$_3$ | H | H | H | H | NC$_2$H$_5$ | |
| I-152 | " | " | " | " | " | NC$_3$H$_7^i$ | |
| I-153 | 2-CH$_3$-3-C$_2$H$_5$-4-SO$_2$CH$_3$ | " | " | " | " | NH | |
| I-154 | " | " | " | " | " | NCH$_3$ | |
| I-155 | 2-CH$_3$-3-C$_3$H$_7^i$-4-SO$_2$CH$_3$ | " | " | " | " | NH | |
| I-156 | " | " | " | " | " | NCH$_3$ | |
| I-157 | 2-CH$_3$-3-CH$_2$OCH$_3$-4-SO$_2$CH$_3$ | " | " | " | " | NH | |
| I-158 | " | " | " | " | " | NCH$_3$ | |
| I-159 | 2-CH$_3$-3-CH$_2$CH$_2$OCH$_3$-4-SO$_2$CH$_3$ | " | " | " | " | NH | |
| I-160 | " | " | " | " | " | NCH$_3$ | |
| I-161 | 2-CH$_3$-3-CH$_2$COOCH$_3$-4-SO$_2$CH$_3$ | " | " | " | " | NH | |
| I-162 | " | " | " | " | " | NCH$_3$ | |
| I-163 | 2-CH$_3$-3-OC$_3$H$_7^i$-4-SO$_2$CH$_3$ | " | " | " | " | NH | |
| I-164 | " | " | " | " | " | NCH$_3$ | |
| I-165 | 2-CH$_3$-3-OC$_4$H$_9^n$-4-SO$_2$CH$_3$ | H | H | H | H | NH | |
| I-166 | " | " | " | " | " | NCH$_3$ | |
| I-167 | " | " | " | " | " | NC$_2$H$_5$ | |
| I-168 | " | " | " | " | " | NC$_3$H$_7^i$ | |
| I-169 | 2-CH$_3$-3-OCH$_2$CH=CH$_2$-4-SO$_2$CH$_3$ | " | " | " | " | NH | |
| I-170 | " | " | " | " | " | NCH$_3$ | |
| I-171 | " | " | " | " | " | NC$_2$H$_5$ | |
| I-172 | " | " | " | " | " | NC$_3$H$_7^i$ | |
| I-173 | 2-CH$_3$-3-OCH$_2$C≡CH-4-SO$_2$CH$_3$ | " | " | " | " | NH | |
| I-174 | " | " | " | " | " | NCH$_3$ | |
| I-175 | " | " | " | " | " | NC$_2$H$_5$ | |
| I-176 | " | " | " | " | " | NC$_3$H$_7^i$ | |
| I-177 | 2-CH$_3$-3-OCH$_2$CH$_2$OCH$_3$-4-SO$_2$CH$_3$ | " | " | " | " | NH | |
| I-178 | " | CH$_3$ | " | " | " | " | |
| I-179 | 2-CH$_3$-3-OCH$_2$CH$_2$OCH$_3$-4-SO$_2$CH$_3$ | H | H | H | CH$_3$ | NH | |
| I-180 | " | " | " | " | H | NCH$_3$ | powder*8 |
| I-181 | " | CH$_3$ | " | " | " | " | |
| I-182 | " | H | " | " | CH$_3$ | " | |
| I-183 | " | " | " | " | H | NC$_2$H$_5$ | |
| I-184 | " | CH$_3$ | " | " | " | " | |
| I-185 | " | H | " | " | CH$_3$ | " | |
| I-186 | " | " | " | " | H | NC$_3$H$_7^i$ | |
| I-187 | 2-CH$_3$-3-OCH$_2$CH$_2$OC$_2$H$_5$-4-SO$_2$CH$_3$ | " | " | " | " | NH | |
| I-188 | " | " | " | " | " | NCH$_3$ | |
| I-189 | 2-CH$_3$-3-OCH$_2$CH=CHCl-4-SO$_2$CH$_3$ | " | " | " | " | NH | |
| I-190 | " | " | " | " | " | NCH$_3$ | |
| I-191 | 2-CH$_3$-3-OCH$_2$CH$_2$SCH$_3$-4-SO$_2$CH$_3$ | " | " | " | " | NH | |
| I-192 | " | " | " | " | " | NCH$_3$ | |
| I-193 | 2-CH$_3$-3-OCH$_2$CH$_2$SCH$_3$-4-SO$_2$CH$_3$ | H | H | H | H | NC$_2$H$_5$ | |
| I-194 | " | " | " | " | " | NC$_3$H$_7^i$ | |
| I-195 | 2-CH$_3$-3-OCH$_2$CH(CH$_3$)OCH$_3$-4-SO$_2$CH$_3$ | " | " | " | " | NH | |
| I-196 | " | " | " | " | " | NCH$_3$ | |
| I-197 | 2-CH$_3$-3-SCH$_3$-4-SO$_2$CH$_3$ | " | " | " | " | NH | |
| I-198 | " | " | " | " | " | NCH$_3$ | |
| I-199 | 2-CH$_2$CH=CH$_2$-3-OCH$_3$-4-SO$_2$CH$_3$ | " | " | " | " | NH | |
| I-200 | " | " | " | " | " | NCH$_3$ | |

TABLE 1-continued

Stuctural formula

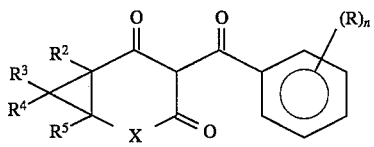

| Compound No. | (R)$_n$ | R$^2$ | R$^3$ | R$^4$ | R$^5$ | X | Physical constant [ ] m.p. °C. |
|---|---|---|---|---|---|---|---|
| I-201 | 3-NO$_2$-4-SCH$_3$ | " | " | " | " | " | |
| I-202 | 3-OCH$_2$CH$_2$OCH$_3$-4-SO$_2$CH$_3$ | " | " | " | " | " | |
| I-203 | 2-Cl-3-OCH$_2$CH$_2$OCH$_3$-4-SO$_2$CH$_3$ | " | " | " | " | O | |
| I-204 | 2-CH$_3$-3-OCH$_2$CH$_2$OCH$_3$-4-SO$_2$CH$_3$ | " | " | " | " | " | |
| I-205 | 2-Cl-3-CO$_2$CH$_3$-4-SO$_2$CH$_3$ | " | " | " | " | " | |
| I-206 | 2-CH$_3$-3-CO$_2$CH$_3$-4-SO$_2$CH$_3$ | " | " | " | " | " | |
| I-207 | 2-NO$_2$-4-Cl | H | H | H | H | S | |
| I-208 | 2-NO$_2$-4-CF$_3$ | " | " | " | " | " | |
| I-209 | 2-NO$_2$-4-SO$_2$CH$_3$ | " | " | " | " | " | |
| I-210 | 2-Cl-4-SO$_2$CH$_3$ | " | " | " | " | " | |
| I-211 | 2,3-Cl$_2$-4-SO$_2$CH$_3$ | " | " | " | " | " | |
| I-212 | 2-Cl-3-CH$_3$-4-SO$_2$CH$_3$ | " | " | " | " | " | |
| I-213 | 2-Cl-3-CO$_2$CH$_3$-4-SO$_2$CH$_3$ | " | " | " | " | " | |
| I-214 | 2-Cl-3-OCH$_3$-4-SO$_2$CH$_3$ | " | " | " | " | " | |
| I-215 | 2-Cl-3-OCH$_2$CH$_2$OCH$_3$-4-SO$_2$CH$_3$ | " | " | " | " | " | |
| I-216 | 2,3-(CH$_3$)$_2$-4-SO$_2$CH$_3$ | " | " | " | " | " | |
| I-217 | 2-CH$_3$-3-Cl-4-SO$_2$CH$_3$ | " | " | " | " | " | |
| I-218 | 2-CH$_3$-3-CO$_2$CH$_3$-4-SO$_2$CH$_3$ | " | " | " | " | " | |
| I-219 | 2-CH$_3$-3-OCH$_3$-4-SO$_2$CH$_3$ | " | " | " | " | " | |
| I-220 | 2-CH$_3$-3-OCH$_2$CH$_2$OCH$_3$-4-SO$_2$CH$_3$ | " | " | " | " | " | |

$^1$H-NMR (CDCl$_3$) δ:ppm
*[1] 1.23(m, 1H), 1.43(m, 1H), 2.16(m, 1H), 3.20(s, 3H), 4.03(s, 3H), 4.49(m, 1H), 7.08(m, 1H), 7.89(m, 1H)
*[2] 2.49(m, 2H), 3.23(s, 3H) 3.63(m, 2H), 3.76(s, 3H), 4.03(s, 3H), 4.69(m, 2H), 6.86(m, 2H), 6.92(m, 1H), 7.29(m, 2H), 7.86(m, 1H)
*[3] 0.89(m, 1H), 1.38(m, 1H), 1.88(m, 1H), 3.03(m, 2H), 3.08(s, 3H), 3.26(s, 3H), 7.43(m, 1H), 8.18(m, 1H), 8.66(m, 1H)
*[4] 1.12(m, 1H), 1.53(m, 1H), 2.05(m, 1H), 3.08(m, 2H), 3.12(s, 3H), 3.31(s, 3H), 7.47(m, 1H), 7.92(m, 1H)
*[5] 1.13(m, 1H), 1.49(m, 1H), 2.04(m, 1H), 2.49(m, 1H), 3.27(s, 3H), 3.42(bs, 3H), 4.10(s, 3H), 6.72(bs, 1H), 7.16(m, 1H), 7.92(m, 1H)
*[6] 0.92(m, 1H), 1.39(m, 1H), 1.91(m, 1H), 2.79(m, 1H), 2.91(s, 3H), 3.13(s, 3H), 4.07(s, 3H), 4.75(m, 2H), 6.87(m, 1H), 7.85(m, 1H)
*[7] 1.09(m, 1H), 1.55(m, 1H), 2.01(m, 1H), 3.20(m, 2H), 3.29(s, 3H), 3.33(s, 3H), 3.46(s, 3H), 3.83(m, 2H), 4.41(m, 2H), 7.16(m, 1H), 7.92(m, 1H)
*[8] 1.06(m, 1H), 1.51(m, 1H), 2.00(m, 1H), 2.26(bs, 3H), 3.12(m, 1H), 3.26(s, 6H), 3.45(s, 3H), 3.83(m, 2H), 4.25(m, 2H), 7.04(bs, 1H), 7.86(bd, 1H)

TABLE 2

Structural formula

| Compound No. | (R)$_n$ | R$^2$ | R$^3$ | R$^4$ | R$^5$ | R$^7$ | X | Physical constant [ ] m.p. °C. |
|---|---|---|---|---|---|---|---|---|
| II-1 | 2-NO$_2$-4-Cl | H | H | H | H | OH | O | [135–137] |
| II-2 | " | " | " | " | " | OCH$_2$–⌬ | " | oil |
| II-3 | " | " | " | " | " | OAc | " | oil |
| II-4 | " | " | " | " | " | OSO$_2$CH$_3$ | " | white crystal |
| II-5 | " | " | " | " | " | I | " | |
| II-6 | " | " | " | " | CH$_3$ | OH | " | [179–180] $n_D^{26}$ 1.5787 |
| II-7 | " | " | " | " | " | OCH$_3$ | " | |
| II-8 | " | " | " | " | " | OCH$_2$–⌬ | " | |
| II-9 | " | " | " | " | " | OAc | " | |
| II-10 | " | " | " | " | " | OSO$_2$CH$_3$ | " | |
| II-11 | " | " | " | " | " | I | " | |
| II-12 | 2-NO$_2$-4-SO$_2$CH$_3$ | " | " | " | H | OH | " | |
| II-13 | " | " | " | " | " | OCH$_2$–⌬ | " | |
| II-14 | " | " | " | " | " | OSO$_2$CH$_3$ | " | |
| II-15 | " | " | " | " | " | OAc | " | |
| II-16 | " | " | " | " | " | I | " | |
| II-17 | " | " | " | " | CH$_3$ | OH | " | |
| II-18 | " | " | " | " | " | OCH$_3$ | " | [131–135] decomposed |

TABLE 2-continued

Structural formula:

R⁴—C(R³)(R⁷)—C(R⁵)—C(=O)—CH(—C(=O)—Ar(R)n)—C(=O)—X (cyclic), where R² is on the ring.

| Compound No. | (R)n | R² | R³ | R⁴ | R⁵ | R⁷ | X | Physical constant [ ] m.p. °C. |
|---|---|---|---|---|---|---|---|---|
| II-19 | " | " | " | " | " | " | OCH₂—Ph | " | |
| II-20 | " | " | " | " | " | OAc | " | |
| II-21 | " | " | " | " | " | OSO₂CH₃ | " | |
| II-22 | " | " | " | " | " | I | " | |
| II-23 | 2,3-(CH₃)₂-4-SO₂CH₃ | " | " | " | H | OH | " | |
| II-24 | " | " | " | " | " | " | OCH₂—Ph | " | |
| II-25 | " | " | " | " | " | OAc | " | |
| II-26 | " | " | " | " | " | OSO₂CH₃ | " | |
| II-27 | " | " | " | " | " | I | " | |
| II-28 | " | " | " | " | " | OH | " | |
| II-29 | 2-Cl-3-OCH₃-4-SO₂CH₃ | " | " | " | " | OCH₂—Ph | " | |
| II-30 | " | " | " | " | " | OAc | " | |
| II-31 | " | " | " | " | " | OSO₂CH₃ | " | |
| II-32 | " | " | " | " | " | I | NCH₃ | $n_D^{25}$ 1.5565 |
| II-33 | 2-NO₂-4-Cl | " | " | " | " | OC₄H₉ⁱ | " | [152–154] |
| II-34 | " | " | " | " | " | OH | " | |
| II-35 | " | " | " | " | " | OCH₃ | " | |
| II-36 | " | " | " | " | " | OC₂H₅ | " | |
| II-37 | " | " | " | " | " | OCOCH₃ | " | |
| II-38 | " | " | " | " | " | OSO₂CH₃ | " | |
| II-39 | " | " | " | " | " | OH | NH | |
| II-40 | " | " | " | " | " | OCH₃ | " | |
| II-41 | " | " | " | " | " | OC₂H₅ | " | |
| II-42 | " | " | " | " | " | OC₄H₉ⁱ | " | |
| II-43 | " | " | " | " | " | OCOCH₃ | " | |
| II-44 | " | " | " | " | " | OSO₂CH₃ | " | |

TABLE 2-continued

Structural formula:

$$R^4\underset{R^7}{\overset{R^3}{>}}R^5 \text{ ... } R^2 \text{ (cyclohexanedione with X and phenyl-}(R)_n\text{ substituent)}$$

| Compound No. | $(R)_n$ | $R^2$ | $R^3$ | $R^4$ | $R^5$ | $R^7$ | X | Physical constant [ ] m.p. °C. |
|---|---|---|---|---|---|---|---|---|
| II-45 | " | " | " | " | " | OH | $NC_2H_5$ | [127–129] |
| II-46 | " | " | " | " | " | $OCH_3$ | " | [128–130] |
| II-47 | " | " | " | " | " | $OC_2H_5$ | " | |
| II-48 | " | " | " | " | " | $OC_4H_9^i$ | " | |
| II-49 | " | " | " | " | " | $OCOCH_3$ | " | |
| II-50 | " | " | " | " | " | $OSO_2CH_3$ | " | |
| II-51 | " | " | " | " | " | OH | $NC_3H_7^i$ | |
| II-52 | " | " | " | " | " | $OCH_3$ | " | |
| II-53 | " | " | " | " | " | $OCOCH_3$ | " | |
| II-54 | " | " | " | " | " | $OSO_2CH_3$ | " | |
| II-55 | " | " | " | " | " | OH | $N-CH_2-\text{(4-}OCH_3\text{-phenyl)}$ | powder*9 |
| II-56 | " | " | " | " | " | $OCH_3$ | " | |
| II-57 | " | " | " | " | " | $OCOCH_3$ | " | |
| II-58 | " | " | " | " | " | $OSO_2CH_3$ | " | |
| II-59 | $2\text{-}NO_2$ | " | " | " | " | OH | NH | |
| II-60 | " | " | " | " | " | $OCH_3$ | " | |
| II-61 | " | " | " | " | " | $OCOCH_3$ | " | |
| II-62 | " | " | " | " | " | $OSO_2CH_3$ | " | |
| II-63 | " | " | " | " | " | OH | $NCH_3$ | [155–157] |
| II-64 | " | " | " | " | " | $OCH_3$ | " | [137–138] |
| II-65 | " | " | " | " | " | $OCOCH_3$ | " | |
| II-66 | " | " | " | " | " | $OSO_2CH_3$ | " | |
| II-67 | $2\text{-}NO_2\text{-}4\text{-}CF_3$ | " | " | " | " | OH | NH | |
| II-68 | " | " | " | " | " | $OCH_3$ | " | |
| II-69 | " | " | " | " | " | $OCOCH_3$ | " | |
| II-70 | " | " | " | " | " | $OSO_2CH_3$ | " | |
| II-71 | " | " | " | " | " | OH | $NCH_3$ | |
| II-72 | " | " | " | " | " | $OCH_3$ | " | |
| II-73 | " | " | " | " | " | $OCOCH_3$ | " | |
| II-74 | " | " | " | " | " | $OSO_2CH_3$ | " | |
| II-75 | " | " | " | " | " | OH | $NC_2H_5$ | |
| II-76 | " | " | " | " | " | $OCH_3$ | " | |
| II-77 | " | " | " | " | " | $OCOCH_3$ | " | |
| II-78 | " | " | " | " | " | $OSO_2CH_3$ | " | |
| II-79 | $2\text{-}NO_2\text{-}4\text{-}SCH_3$ | " | " | " | " | OH | NH | powder*10 |

TABLE 2-continued

Structural formula:

$$R^2, R^3, R^4, R^5, R^7 \text{ substituted ring with } X, \text{ phenyl}(R)_n$$

| Compound No. | $(R)_n$ | $R^2$ | $R^3$ | $R^4$ | $R^5$ | $R^7$ | X | Physical constant [ ] m.p. °C. |
|---|---|---|---|---|---|---|---|---|
| II-80 | " | " | " | " | " | $OCH_3$ | " | |
| II-81 | " | " | " | " | " | $OCOCH_3$ | " | |
| II-82 | " | " | " | " | " | $OSO_2CH_3$ | " | |
| II-83 | " | " | " | " | " | $OH$ | $NCH_3$ | |
| II-84 | " | " | " | " | " | $OCH_3$ | " | |
| II-85 | " | " | " | " | " | $OC_4H_9^t$ | " | powder*11 $n_D^{26}$ 1.6242 |
| II-86 | " | " | " | " | " | $OCOCH_3$ | " | |
| II-87 | " | " | " | " | " | $OSO_2CH_3$ | " | |
| II-88 | " | " | " | " | " | $OH$ | $NC_2H_5$ | |
| II-89 | " | " | " | " | " | $OCH_3$ | " | |
| II-90 | " | " | " | " | " | $OC_4H_9^t$ | " | |
| II-91 | " | " | " | " | " | $OCOCH_3$ | " | |
| II-92 | $2\text{-}NO_2\text{-}4\text{-}SOCH_3$ | " | " | " | " | $OSO_2CH_3$ | $NH$ | |
| II-93 | " | " | " | " | " | $OH$ | " | |
| II-94 | " | " | " | " | " | $OCH_3$ | " | |
| II-95 | " | " | " | " | " | $OC_4H_9^t$ | " | |
| II-96 | " | " | " | " | " | $OCOCH_3$ | $NCH_3$ | |
| II-97 | " | " | " | " | " | $OSO_2CH_3$ | " | |
| II-98 | " | " | " | " | " | $OH$ | " | |
| II-99 | " | " | " | " | " | $OCH_3$ | " | |
| II-100 | " | " | " | " | " | $OC_4H_9^t$ | " | |
| II-101 | " | " | " | " | " | $OCOCH_3$ | " | |
| II-102 | $2\text{-}NO_2\text{-}4\text{-}SO_2CH_3$ | " | " | " | " | $OSO_2CH_3$ | $NH$ | |
| II-103 | " | " | " | " | " | $OH$ | " | |
| II-104 | " | " | " | " | " | $OCH_3$ | " | |
| II-105 | " | " | " | " | " | $OC_4H_9^t$ | " | |
| II-106 | " | " | " | " | " | $OCOCH_3$ | " | |
| II-107 | " | " | " | " | " | $OSO_2CH_3$ | " | |
| II-108 | " | " | " | " | " | $OH$ | $NCH_3$ | [149-151] |
| II-109 | " | " | " | " | " | $OCH_3$ | " | |
| II-110 | " | " | " | " | " | $OC_4H_9^t$ | " | $n_D^{25}$ 1.5595 |
| II-111 | " | " | " | " | " | $OCOCH_3$ | " | |
| II-112 | " | " | " | " | " | $OSO_2CH_3$ | " | |
| II-113 | " | " | " | " | " | $OH$ | $NC_2H_5$ | |
| II-114 | " | " | " | " | " | $OCH_3$ | " | |
| II-115 | " | " | " | " | " | $OC_4H_9^t$ | " | |
| II-116 | " | " | " | " | " | $OCOCH_3$ | " | |
| II-117 | " | " | " | " | " | $OSO_2CH_3$ | " | |
| II-118 | $2,4\text{-}Cl_2$ | " | " | " | " | $OH$ | $NH$ | |
| II-119 | " | " | " | " | " | $OCH_3$ | " | |
| II-120 | " | " | " | " | " | $OCOCH_3$ | " | |

TABLE 2-continued

Structural formula

| Compound No. | (R)n | R² | R³ | R⁴ | R⁵ | R⁷ | X | Physical constant [ ] m.p. °C. |
|---|---|---|---|---|---|---|---|---|
| II-121 | " | " | " | " | " | OSO₂CH₃ | NCH₃ | |
| II-122 | " | " | " | " | " | OH | " | |
| II-123 | " | " | " | " | " | OCH₃ | " | |
| II-124 | " | " | " | " | " | OCOCH₃ | " | |
| II-125 | " | " | " | " | " | OSO₂CH₃ | " | |
| II-126 | 3,4-Cl₂ | " | " | " | " | OH | NH | |
| II-127 | " | " | " | " | " | OCH₃ | " | |
| II-128 | " | " | " | " | " | OCOCH₃ | " | |
| II-129 | " | " | " | " | " | OSO₂CH₃ | " | |
| II-130 | " | " | " | " | " | OH | NCH₃ | $n_D^{27.6}$ 1.6004 |
| II-131 | " | " | " | " | " | OCH₃ | " | powder |
| II-132 | " | " | " | " | " | OCOCH₃ | " | |
| II-133 | " | " | " | " | " | OSO₂CH₃ | " | |
| II-134 | 2-Cl-4-SO₂CH₃ | " | " | " | " | OH | NH | |
| II-135 | " | " | " | " | " | OCH₃ | " | |
| II-136 | " | " | " | " | " | OCOCH₃ | " | |
| II-137 | " | " | " | " | " | OSO₂CH₃ | " | |
| II-138 | " | " | " | " | " | OH | NCH₃ | [170–171] |
| II-139 | " | " | " | " | " | OCH₃ | " | $n_D^{26}$ 1.5800 |
| II-140 | " | " | " | " | " | OCOCH₃ | " | |
| II-141 | " | " | " | " | " | OSO₂CH₃ | " | |
| II-142 | " | " | " | " | " | OH | NC₂H₅ | |
| II-143 | " | " | " | " | " | OCH₃ | " | |
| II-144 | " | " | " | " | " | OCOCH₃ | " | |
| II-145 | " | " | " | " | " | OSO₂CH₃ | " | |
| II-146 | 2,3-Cl₂-4-SO₂CH₃ | " | " | " | " | OH | NH | |
| II-147 | " | " | " | " | " | OCH₃ | " | |
| II-148 | " | " | " | " | " | OCOCH₃ | " | |
| II-149 | " | " | " | " | " | OSO₂CH₃ | " | |
| II-150 | " | " | " | " | " | OH | NCH₃ | |
| II-151 | " | " | " | " | " | OCH₃ | " | |
| II-152 | " | " | " | " | " | OCOCH₃ | " | |
| II-153 | " | " | " | " | " | OSO₂CH₃ | " | |
| II-154 | " | " | " | " | " | OH | NC₂H₅ | |
| II-155 | " | " | " | " | " | OCH₃ | " | |
| II-156 | " | " | " | " | " | OCOCH₃ | " | |
| II-157 | " | " | " | " | " | OSO₂CH₃ | " | |
| II-158 | " | " | " | " | " | OH | NC₃H₇$^i$ | |
| II-159 | " | " | " | " | " | OCH₃ | " | |
| II-160 | " | " | " | " | " | OCOCH₃ | " | |
| II-161 | " | " | " | " | " | OSO₂CH₃ | " | |

TABLE 2-continued

Structural formula

R²—(R³R⁴)(R⁷R⁵)—C(=O)—C(=O)—X—C(=O)—Ar(R)ₙ

| Compound No. | (R)ₙ | R² | R³ | R⁴ | R⁵ | R⁷ | X | Physical constant [ ] m.p. °C. |
|---|---|---|---|---|---|---|---|---|
| II-162 | 2-Cl-3-CH₃-4-SO₂CH₃ | " | " | " | " | OH | NH | |
| II-163 | " | " | " | " | " | OCH₃ | " | |
| II-164 | " | " | " | " | " | OCOCH₃ | " | |
| II-165 | " | " | " | " | " | OSO₂CH₃ | " | |
| II-166 | " | " | " | " | " | OH | NCH₃ | |
| II-167 | " | " | " | " | " | OCH₃ | " | |
| II-168 | " | " | " | " | " | OCOCH₃ | " | |
| II-169 | " | " | " | " | " | OSO₂CH₃ | " | |
| II-170 | " | " | " | " | " | OH | NC₂H₅ | |
| II-171 | " | " | " | " | " | OCH₃ | " | |
| II-172 | " | " | " | " | " | OCOCH₃ | " | |
| II-173 | " | " | " | " | " | OSO₂CH₃ | " | |
| II-174 | " | " | " | " | " | OH | NC₃H₇ⁱ | |
| II-175 | " | " | " | " | " | OCH₃ | " | |
| II-176 | " | " | " | " | " | OCOCH₃ | " | |
| II-177 | " | " | " | " | " | OSO₂CH₃ | " | |
| II-178 | 2-Cl-3-C₂H₅-4-SO₂CH₃ | " | " | " | " | OH | NH | |
| II-179 | " | " | " | " | " | OCH₃ | " | |
| II-180 | " | " | " | " | " | OCOCH₃ | NCH₃ | |
| II-181 | " | " | " | " | " | OSO₂CH₃ | " | |
| II-182 | 2-Cl-3-C₃H₇ⁱ-4-SO₂CH₃ | " | " | " | " | OH | NH | |
| II-183 | " | " | " | " | " | OCH₃ | " | |
| II-184 | " | " | " | " | " | OCOCH₃ | NCH₃ | |
| II-185 | " | " | " | " | " | OSO₂CH₃ | " | |
| II-186 | 2-Cl-3-CH₂OCH₂CH₂OCH₃-4-SO₂CH₃ | " | " | " | " | OH | NH | |
| II-187 | " | " | " | " | " | OCH₃ | " | |
| II-188 | " | " | " | " | " | OCOCH₃ | NCH₃ | |
| II-189 | " | " | " | " | " | OSO₂CH₃ | " | |
| II-190 | " | " | " | " | " | OH | NH | |
| II-191 | " | " | " | " | " | OCH₃ | " | |
| II-192 | " | " | " | " | " | OCOCH₃ | NCH₃ | |
| II-193 | " | " | " | " | " | OSO₂CH₃ | " | |
| II-194 | " | " | " | " | " | OH | NH | powder*12 |
| II-195 | " | " | " | " | " | OCH₃ | " | |
| II-196 | " | " | " | " | " | OCOCH₃ | NCH₃ | |
| II-197 | " | " | " | " | " | OSO₂CH₃ | " | |
| II-198 | " | " | " | " | " | OH | NH | |
| II-199 | " | " | " | " | " | OCH₃ | " | |
| II-200 | " | " | " | " | " | OCOCH₃ | NCH₃ | |
| II-201 | " | " | " | " | " | OSO₂CH₃ | " | |
| II-202 | " | " | " | " | " | OH | NC₂H₅ | |

TABLE 2-continued

Structural formula

| Compound No. | (R)ₙ | R² | R³ | R⁴ | R⁵ | R⁷ | X | Physical constant [ ] m.p. °C. |
|---|---|---|---|---|---|---|---|---|
| II-203 | " | " | " | " | " | OCH₃ | " | |
| II-204 | " | " | " | " | " | OCOCH₃ | " | |
| II-205 | " | " | " | " | " | OSO₂CH₃ | " | |
| II-206 | " | " | " | " | " | OH | NC₃H₇¹ | |
| II-207 | " | " | " | " | " | OCH₃ | " | |
| II-208 | " | " | " | " | " | OCOCH₃ | " | |
| II-209 | " | " | " | " | " | OSO₂CH₃ | " | |
| II-210 | 2-Cl-3-CH₂OCH₃-4-SO₂CH₃ | " | " | " | " | OH | NH | |
| II-211 | " | " | " | " | " | OCH₃ | " | |
| II-212 | " | " | " | " | " | OCOCH₃ | " | |
| II-213 | " | " | " | " | " | OSO₂CH₃ | " | |
| II-214 | " | " | " | " | " | OH | NCH₃ | |
| II-215 | " | " | " | " | " | OCH₃ | " | |
| II-216 | " | " | " | " | " | OCOCH₃ | " | |
| II-217 | " | " | " | " | " | OSO₂CH₃ | " | |
| II-218 | 2-Cl-3-CH₂CH₂OCH₃-4-SO₂CH₃ | " | " | " | " | OH | NH | |
| II-219 | " | " | " | " | " | OCH₃ | " | |
| II-220 | " | " | " | " | " | OCOCH₃ | " | |
| II-221 | " | " | " | " | " | OSO₂CH₃ | " | |
| II-222 | " | " | " | " | " | OH | NCH₃ | |
| II-223 | " | " | " | " | " | OCH₃ | " | |
| II-224 | " | " | " | " | " | OCOCH₃ | " | |
| II-225 | " | " | " | " | " | OSO₂CH₃ | " | |
| II-226 | 2-Cl-3-CH₂CO₂CH₃-4-SO₂CH₃ | " | " | " | " | OH | NH | |
| II-227 | " | " | " | " | " | OCH₃ | " | |
| II-228 | " | " | " | " | " | OCOCH₃ | " | |
| II-229 | " | " | " | " | " | OSO₂CH₃ | " | |
| II-230 | " | " | " | " | " | OH | NCH₃ | |
| II-231 | " | " | " | " | " | OCH₃ | " | |
| II-232 | " | " | " | " | " | OCOCH₃ | " | |
| II-233 | " | " | " | " | " | OSO₂CH₃ | " | |
| II-234 | 2-Cl-3-CO₂CH₃-4-SO₂CH₃ | H | " | H | " | OH | NH | |
| II-235 | 2-Cl-3-CO₂CH₃-4-SO₂CH₃ | " | H | H | H | OCH₃ | NH | |
| II-236 | " | " | " | " | " | OCOCH₃ | " | |
| II-237 | " | " | " | " | " | OSO₂CH₃ | " | |
| II-238 | " | " | " | " | " | OH | NCH₃ | |
| II-239 | " | " | " | " | " | OCH₃ | " | |
| II-240 | " | " | " | " | " | OCOCH₃ | " | |
| II-241 | " | CH₃ | " | " | " | OSO₂CH₃ | " | |
| II-242 | " | " | " | " | " | OH | " | |
| II-243 | " | " | " | " | " | OCH₃ | " | powder*¹³ |

TABLE 2-continued

Structural formula:

R⁴-R³-R²-...-R⁵-R⁷-X with phenyl (R)ₙ and two C=O groups

| Compound No. | (R)ₙ | R² | R³ | R⁴ | R⁵ | R⁷ | X | Physical constant [ ] m.p. °C. |
|---|---|---|---|---|---|---|---|---|
| II-244 | " | " | " | " | " | OCOCH₃ | " | |
| II-245 | " | " | " | " | " | OSO₂CH₃ | " | |
| II-246 | " | H | " | " | " | OH | " | |
| II-247 | " | " | " | " | " | OCH₃ | " | |
| II-248 | " | " | " | " | " | OCOCH₃ | " | |
| II-249 | " | " | " | " | " | OSO₂CH₃ | " | |
| II-250 | " | " | " | " | " | OH | NC₂H₅ | |
| II-251 | " | " | " | " | " | OCH₃ | " | |
| II-252 | " | " | " | " | " | OCOCH₃ | " | |
| II-253 | " | " | " | " | " | OSO₂CH₃ | " | |
| II-254 | " | CH₃ | " | " | CH₃ | OH | " | |
| II-255 | " | " | " | " | " | OCH₃ | " | |
| II-256 | " | " | " | " | " | OCOCH₃ | " | |
| II-257 | " | " | " | " | " | OSO₂CH₃ | " | |
| II-258 | " | H | " | " | H | OH | " | |
| II-259 | " | " | " | " | " | OCH₃ | " | |
| II-260 | " | " | " | " | " | OCOCH₃ | " | |
| II-261 | " | " | " | " | " | OSO₂CH₃ | " | |
| II-262 | " | " | " | " | " | OH | NC₃H₇ⁱ | |
| II-263 | " | " | " | " | " | OCH₃ | " | |
| II-264 | " | " | " | " | " | OCOCH₃ | " | |
| II-265 | " | " | " | " | " | OSO₂CH₃ | " | |
| II-266 | 2-Cl-3-OCH₃-4-SO₂CH₃ | CH₃ | " | " | CH₃ | OH | NH | powder*14 [128–129] |
| II-267 | " | " | " | " | " | OCH₃ | " | |
| II-268 | " | " | " | " | " | OC₄H₉ᵗ | " | |
| II-269 | " | " | " | " | " | OCOCH₃ | " | |
| II-270 | " | " | " | " | " | OSO₂CH₃ | " | |
| II-271 | " | CH₃ | " | " | CH₃ | OH | " | |
| II-272 | " | " | " | " | " | OCH₃ | " | |
| II-273 | " | " | " | " | " | OC₄H₉ᵗ | " | |
| II-274 | " | " | " | " | " | OCOCH₃ | " | |
| II-275 | " | " | " | " | " | OSO₂CH₃ | " | |
| II-276 | " | H | " | " | CH₃ | OH | " | |
| II-277 | " | " | " | " | " | OCH₃ | " | |
| II-278 | " | " | " | " | " | OC₄H₉ᵗ | " | |
| II-279 | " | " | " | " | " | OCOCH₃ | " | |
| II-280 | " | " | " | " | " | OSO₂CH₃ | " | |
| II-281 | " | H | " | " | H | OH | NCH₃ | [189–191] |
| II-282 | " | " | " | " | " | OCH₃ | " | $n_D^{25}$ 1.5502 |
| II-283 | " | " | " | " | " | OC₄H₉ᵗ | " | |
| II-284 | " | " | " | " | " | OCOCH₃ | " | |

TABLE 2-continued

Structural formula $$\begin{array}{c} R^4 \underset{R^7}{\overset{R^3}{\diagdown}} R^5 \\ \end{array}$$ (with ring containing R², R³, R⁴, R⁵, X, carbonyls, and phenyl-$(R)_n$ group)

| Compound No. | (R)ₙ | R² | R³ | R⁴ | R⁵ | R⁷ | X | Physical constant [ ] m.p. °C. |
|---|---|---|---|---|---|---|---|---|
| II-285 | " | CH₃ | " | " | " | OSO₂CH₃ | " | |
| II-286 | " | " | " | " | " | OH | " | |
| II-287 | " | " | " | " | " | OCH₃ | " | |
| II-288 | " | " | " | " | " | OC₄H₉ᵗ | " | |
| II-289 | " | " | " | " | " | OCOCH3 | " | |
| II-290 | " | " | " | " | " | OCOCH₃ | " | |
| II-291 | " | " | " | " | CH₃ | OSO₂CH₃ | " | |
| II-292 | " | H | " | " | " | OH | " | |
| II-293 | " | " | " | " | " | OCH₃ | " | |
| II-294 | " | " | " | " | " | OC₄H₉ᵗ | " | |
| II-295 | " | " | " | " | " | OCOCH₃ | " | |
| II-296 | " | " | " | " | " | OSO₂CH₃ | " | |
| II-297 | " | " | " | " | H | OH | NC₂H₅ | powder*15 |
| II-298 | " | " | " | " | " | OCH₃ | " | powder*16 |
| II-299 | " | " | " | " | " | OC₄H₉ᵗ | " | |
| II-300 | " | " | " | " | " | OCOCH₃ | " | |
| II-301 | " | " | " | " | " | OSO₂CH₃ | " | |
| II-302 | " | CH₃ | " | " | CH₃ | OH | " | |
| II-303 | " | " | " | " | " | OCH₃ | " | |
| II-304 | " | " | " | " | " | OC₄H₉ᵗ | " | |
| II-305 | " | " | " | " | " | OCOCH₃ | " | |
| II-306 | " | " | " | " | " | OSO₂CH₃ | " | |
| II-307 | " | H | " | " | H | OH | " | |
| II-308 | " | " | " | " | " | OCH₃ | " | |
| II-309 | " | " | " | " | " | OC₄H₉ᵗ | " | |
| II-310 | " | " | " | " | " | OCOCH₃ | " | |
| II-311 | " | " | " | " | " | OSO₂CH₃ | " | |
| II-312 | " | " | " | " | H | OH | NC₃H₇ⁱ | |
| II-313 | " | " | " | " | " | OCH₃ | " | |
| II-314 | " | " | " | " | " | OC₄H₉ᵗ | " | |
| II-315 | " | " | " | " | " | OCOCH₃ | " | |
| II-316 | " | " | " | " | " | OSO₂CH₃ | " | |
| II-317 | " | CH₃ | " | " | CH₃ | OH | " | |
| II-318 | " | " | " | " | " | OCH₃ | " | |
| II-319 | " | " | " | " | " | OC₄H₉ᵗ | " | |
| II-320 | " | " | " | " | " | OCOCH₃ | " | |
| II-321 | " | " | " | " | " | OSO₂CH₃ | " | |
| II-322 | " | H | " | " | H | OH | " | |
| II-323 | " | " | " | " | " | OCH₃ | " | |
| II-324 | " | " | " | " | " | OC₄H₉ᵗ | " | |

TABLE 2-continued

Structural formula:

R⁴–C(R³)(R⁷)–C(R⁵)–... ring with X, (R)n on phenyl, two C=O groups

| Compound No. | (R)ₙ | R² | R³ | R⁴ | R⁵ | R⁷ | X | Physical constant [ ] m.p. °C. |
|---|---|---|---|---|---|---|---|---|
| II-325 | " | " | " | " | " | OSO₂CH₃ | " | |
| II-326 | " | " | " | " | H | OH | NCH₂–C₆H₄–OCH₃ | powder*17 |
| II-327 | " | " | " | " | " | OCH₃ | " | |
| II-328 | " | " | " | " | " | OC₄H₉ⁱ | " | |
| II-329 | " | " | " | " | " | OCOCH₃ | " | |
| II-330 | " | " | " | " | " | OSO₂CH₃ | " | |
| II-331 | 2-Cl-3-OC₄H₉ⁿ-4-SO₂CH₃ | " | " | " | " | OH | NH | |
| II-332 | " | " | " | " | " | OCH₃ | " | |
| II-333 | " | " | " | " | " | OCOCH₃ | " | |
| II-334 | " | " | " | " | " | OSO₂CH₃ | " | |
| II-335 | " | " | " | " | " | OH | NCH₃ | |
| II-336 | " | " | " | " | " | OCH₃ | " | |
| II-337 | " | " | " | " | " | OCOCH₃ | " | |
| II-338 | " | " | " | " | " | OSO₂CH₃ | " | |
| II-339 | " | " | " | " | " | OH | NC₂H₅ | |
| II-340 | " | " | " | " | " | OCH₃ | " | |
| II-341 | " | " | " | " | " | OCOCH₃ | " | |
| II-342 | " | " | " | " | " | OSO₂CH₃ | " | |
| II-343 | " | " | " | " | " | OH | NC₃H₇ⁱ | |
| II-344 | " | " | " | " | " | OCH₃ | " | |
| II-345 | " | " | " | " | " | OCOCH₃ | " | |
| II-346 | " | " | " | " | " | OSO₂CH₃ | " | |
| II-347 | 2-Cl-3-OCH₂CH=CH₂-4-SO₂CH₃ | " | " | " | " | OH | NH | powder*18 |
| II-348 | " | " | " | " | " | OCH₃ | " | |
| II-349 | " | " | " | " | " | OCOCH₃ | " | |
| II-350 | " | " | " | " | " | OSO₂CH₃ | " | |
| II-351 | " | CH₃ | " | " | " | OH | NCH₃ | |
| II-352 | " | " | " | " | " | OCH₃ | " | |
| II-353 | " | " | " | " | " | OCOCH₃ | " | |
| II-354 | " | " | " | " | " | OSO₂CH₃ | " | |
| II-355 | " | H | " | " | " | OH | " | |
| II-356 | " | " | " | " | " | OCH₃ | " | |
| II-357 | " | " | " | " | " | OCOCH₃ | " | |
| II-358 | " | " | " | " | " | OSO₂CH₃ | " | |
| II-359 | " | CH₃ | " | " | " | OH | " | powder*19 |

TABLE 2-continued

Structural formula:

$$R^4 \overset{R^3}{\underset{R^7}{\diagup}} \overset{R^2}{\underset{R^5}{\diagdown}} \text{with } O, O, X, \text{ and phenyl}(R)_n$$

| Compound No. | $(R)_n$ | $R^2$ | $R^3$ | $R^4$ | $R^5$ | $R^7$ | X | Physical constant [ ] m.p. °C. |
|---|---|---|---|---|---|---|---|---|
| II-360 | " | " | " | " | " | $OCH_3$ | " | |
| II-361 | " | " | " | " | " | $OCOCH_3$ | " | |
| II-362 | " | " | " | " | " | $OSO_2CH_3$ | " | |
| II-363 | 2-Cl-3-$OCH_2C\equiv CH$-4-$SO_2CH_3$ | H | " | " | " | OH | NH | |
| II-364 | " | " | " | " | " | $OCH_3$ | " | |
| II-365 | " | " | " | " | " | $OCOCH_3$ | " | |
| II-366 | " | " | " | " | " | $OSO_2CH_3$ | " | |
| II-367 | " | $CH_3$ | " | " | " | OH | " | |
| II-368 | " | " | " | " | " | $OCH_3$ | " | |
| II-369 | " | " | " | " | " | $OCOCH_3$ | " | |
| II-370 | " | " | " | " | " | $OSO_2CH_3$ | " | |
| II-371 | " | H | " | " | $CH_3$ | OH | " | |
| II-372 | " | " | " | " | " | $OCH_3$ | " | |
| II-373 | " | " | " | " | " | $OCOCH_3$ | " | |
| II-374 | " | " | " | " | " | $OSO_2CH_3$ | " | |
| II-375 | " | H | " | " | H | OH | " | |
| II-376 | " | " | " | " | " | $OCH_3$ | $NCH_3$ | powder*20 |
| II-377 | " | " | " | " | " | $OCOCH_3$ | " | |
| II-378 | " | " | " | " | " | $OSO_2CH_3$ | " | |
| II-379 | " | $CH_3$ | " | " | $CH_3$ | OH | " | |
| II-380 | " | " | " | " | " | $OCH_3$ | " | |
| II-381 | " | " | " | " | " | $OCOCH_3$ | " | |
| II-382 | " | " | " | " | " | $OSO_2CH_3$ | " | |
| II-383 | " | H | " | " | H | OH | " | |
| II-384 | " | " | " | " | " | $OCH_3$ | " | |
| II-385 | " | " | " | " | " | $OCOCH_3$ | " | |
| II-386 | " | " | " | " | " | $OSO_2CH_3$ | " | |
| II-387 | " | $CH_3$ | " | " | H | OH | $NC_2H_5$ | |
| II-388 | " | " | " | " | " | $OCH_3$ | " | |
| II-389 | " | " | " | " | " | $OCOCH_3$ | " | |
| II-390 | " | " | " | " | " | $OSO_2CH_3$ | " | |
| II-391 | " | $CH_3$ | " | " | " | OH | " | |
| II-392 | " | " | " | " | " | $OCH_3$ | " | |
| II-393 | " | " | " | " | " | $OCOCH_3$ | " | |
| II-394 | " | " | " | " | " | $OSO_2CH_3$ | " | |
| II-395 | " | H | " | " | " | OH | $NC_3H_7^i$ | |
| II-396 | " | " | " | " | " | $OCH_3$ | " | |
| II-397 | " | " | " | " | " | $OCOCH_3$ | " | |
| II-398 | " | " | " | " | " | $OSO_2CH_3$ | " | |
| II-399 | 2-Cl-3-$OC_3H_7^i$-4-$SO_2CH_3$ | " | " | " | " | OH | NH | |

TABLE 2-continued

Structural formula:

R⁴-R³-R²...C(O)-CH(R⁵)-C(O)-R⁷(with (R)n phenyl), with X in ring

| Compound No. | (R)n | R² | R³ | R⁴ | R⁵ | R⁷ | X | Physical constant [ ] m.p. °C. |
|---|---|---|---|---|---|---|---|---|
| II-400 | | | | | | OCH₃ | | |
| II-401 | " | " | " | " | " | OCOCH₃ | " | |
| II-402 | " | " | " | " | " | OSO₂CH₃ | " | |
| II-403 | " | " | " | " | " | OH | NCH₃ | |
| II-404 | " | " | " | " | " | OCH₃ | " | |
| II-405 | " | " | " | " | " | OCOCH₃ | " | |
| II-406 | 2-Cl-3-OCH₂CH₂OCH₃-4-SO₂CH₃ | " | " | " | " | OSO₂CH₃ | " | |
| II-407 | " | " | " | " | " | OH | NH | |
| II-408 | " | " | " | " | " | OCH₃ | " | |
| II-409 | " | " | " | " | " | OCOCH₃ | " | |
| II-410 | " | " | " | " | " | OSO₂CH₃ | " | |
| II-411 | " | CH₃ | " | " | " | OH | " | |
| II-412 | " | " | " | " | " | OCH₃ | " | |
| II-413 | " | " | " | " | " | OCOCH₃ | " | |
| II-414 | " | " | " | " | " | OSO₂CH₃ | " | |
| II-415 | " | H | " | " | CH₃ | OH | " | |
| II-416 | " | " | " | " | " | OCH₃ | " | |
| II-417 | " | " | " | " | " | OCOCH₃ | " | |
| II-418 | " | " | " | " | " | OSO₂CH₃ | " | |
| II-419 | " | CH₃ | " | " | H | OH | NCH₃ | powder*21 |
| II-420 | " | " | " | " | " | OCH₃ | " | powder*22 |
| II-421 | " | " | " | " | " | OCOCH₃ | " | powder*23 |
| II-422 | " | " | " | " | " | OSO₂CH₃ | " | |
| II-423 | " | H | " | " | CH₃ | OH | " | powder*24 |
| II-424 | " | " | " | " | " | OCH₃ | " | |
| II-425 | " | " | " | " | " | OCOCH₃ | " | |
| II-426 | " | " | " | " | " | OSO₂CH₃ | " | |
| II-427 | " | CH₃ | " | " | H | OH | " | |
| II-428 | " | " | " | " | " | OCH₃ | " | |
| II-429 | " | " | " | " | " | OCOCH₃ | " | |
| II-430 | " | " | " | " | " | OSO₂CH₃ | " | |
| II-431 | " | H | " | " | CH₃ | OH | NC₂H₅ | powder*25 |
| II-432 | " | " | " | " | " | OCH₃ | " | |
| II-433 | " | " | " | " | " | OCOCH₃ | " | |
| II-434 | " | " | " | " | " | OSO₂CH₃ | " | |
| II-435 | " | CH₃ | " | " | H | OH | " | |
| II-436 | " | " | " | " | " | OCH₃ | " | |
| II-437 | " | " | " | " | " | OCOCH₃ | " | |
| II-438 | " | " | " | " | " | OSO₂CH₃ | " | |
| II-439 | " | H | " | " | CH₃ | OH | " | |
| II-440 | " | " | " | " | " | OCH₃ | " | |

TABLE 2-continued

Structural formula:

$$\begin{array}{c} R^2 \\ R^3 \\ R^4 \\ R^7 \end{array} \quad R^5 \text{ with carbonyls and } (R)_n \text{ phenyl}$$

| Compound No. | (R)n | R² | R³ | R⁴ | R⁵ | R⁷ | X | Physical constant [ ] m.p. °C. |
|---|---|---|---|---|---|---|---|---|
| II-441 | " | " | " | " | " | OCOCH₃ | " | |
| II-442 | " | " | " | " | " | OSO₂CH₃ | " | |
| II-443 | " | " | " | " | H | OH | " | |
| II-444 | " | " | " | " | " | OCH₃ | NC₃H₇ⁱ | [138–141] |
| II-445 | " | " | " | " | " | OCOCH₃ | " | |
| II-446 | " | " | " | " | " | OSO₂CH₃ | " | |
| II-447 | 2-Cl-3-OCH₂CH₂SCH₃-4-SO₂CH₃ | " | " | " | " | OH | NH | |
| II-448 | " | " | " | " | " | OCH₃ | " | |
| II-449 | " | " | " | " | " | OCOCH₃ | " | |
| II-450 | " | " | " | " | " | OSO₂CH₃ | " | |
| II-451 | " | " | " | " | " | OH | NCH₃ | |
| II-452 | " | " | " | " | " | OCH₃ | " | powder*²⁶ |
| II-453 | " | " | " | " | " | OCOCH₃ | " | |
| II-454 | " | " | " | " | " | OSO₂CH₃ | " | |
| II-455 | " | " | " | " | " | OH | NC₂H₅ | |
| II-456 | " | " | " | " | " | OCH₃ | " | |
| II-457 | " | " | " | " | " | OCOCH₃ | " | |
| II-458 | " | " | " | " | " | OSO₂CH₃ | " | |
| II-459 | " | " | " | " | " | OH | NC₃H₇ⁱ | |
| II-460 | " | " | " | " | " | OCH₃ | " | |
| II-461 | " | " | " | " | " | OCOCH₃ | " | |
| II-462 | " | " | " | " | " | OSO₂CH₃ | " | |
| II-463 | 2-Cl-3-OCH₂CH₂OCH₃-4-SO₂CH₃ | " | " | " | " | OH | NH | |
| II-464 | " | " | " | " | " | OCH₃ | " | |
| II-465 | " | " | " | " | " | OCOCH₃ | " | |
| II-466 | " | " | " | " | " | OSO₂CH₃ | " | |
| II-467 | " | " | " | " | " | OH | NCH₃ | |
| II-468 | " | " | " | " | " | OCH₃ | " | |
| II-469 | " | " | " | " | " | OCOCH₃ | " | |
| II-470 | " | " | " | " | " | OSO₂CH₃ | " | |
| II-471 | " | " | " | H | " | OH | NC₂H₅ | |
| II-472 | " | H | " | H | H | OCOCH₃ | NC₂H₅ | |
| II-473 | 2-Cl-3-OCH₂CH₂OCH₃-4-SO₂CH₃ | " | " | " | " | OCOCH₃ | NC₂H₅ | |
| II-474 | " | " | " | " | " | OSO₂CH₃ | " | |
| II-475 | " | " | " | " | " | OH | NC₃H₇ⁱ | |
| II-476 | " | " | " | " | " | OCH₃ | " | |
| II-477 | " | " | " | " | " | OCOCH₃ | " | |
| II-478 | " | " | " | " | " | OSO₂CH₃ | " | |
| II-479 | 2-Cl-3-OCH₂CH=CHCl-4-SO₂CH₃ | " | " | " | " | OH | NH | |
| II-480 | " | " | " | " | " | OCH₃ | " | |
| II-481 | " | " | " | " | " | OCOCH₃ | " | |

TABLE 2-continued

Structural formula

| Compound No. | (R)n | R2 | R3 | R4 | R5 | R7 | X | Physical constant [ ] m.p. °C. |
|---|---|---|---|---|---|---|---|---|
| II-482 | " | " | " | " | " | OSO₂CH₃ | " | |
| II-483 | " | " | " | " | " | OH | NCH₃ | |
| II-484 | " | " | " | " | " | OCH₃ | " | |
| II-485 | " | " | " | " | " | OCOCH₃ | " | |
| II-486 | " | " | " | " | " | OSO₂CH₃ | " | |
| II-487 | 2-Cl-3-OCH₂CH₂OC₂H₅-4-SO₂CH₃ | " | " | " | " | OH | NH | |
| II-488 | " | " | " | " | " | OCH₃ | " | |
| II-489 | " | " | " | " | " | OCOCH₃ | " | |
| II-490 | " | " | " | " | " | OSO₂CH₃ | " | |
| II-491 | " | " | " | " | " | OH | NCH₃ | |
| II-492 | " | " | " | " | " | OCH₃ | " | |
| II-493 | " | " | " | " | " | OCOCH₃ | " | |
| II-494 | " | " | " | " | " | OSO₂CH₃ | " | |
| II-495 | 2-Cl-3-OCH₂CH(CH₃)OCH₃-4-SO₂CH₃ | " | " | " | " | OH | NH | |
| II-496 | " | " | " | " | " | OCH₃ | " | |
| II-497 | " | " | " | " | " | OCOCH₃ | " | |
| II-498 | " | " | " | " | " | OSO₂CH₃ | " | |
| II-499 | " | " | " | " | " | OH | NCH₃ | |
| II-500 | " | " | " | " | " | OCH₃ | " | |
| II-501 | " | " | " | " | " | OCOCH₃ | " | |
| II-502 | " | " | " | " | " | OSO₂CH₃ | " | |
| II-503 | 2-Cl-3-SCH₃-4-SO₂CH₃ | " | " | " | " | OH | NH | |
| II-504 | " | " | " | " | " | OCOCH₃ | " | |
| II-505 | " | " | " | " | " | OSO₂CH₃ | " | |
| II-506 | " | " | " | " | " | OH | NCH₃ | |
| II-507 | " | " | " | " | " | OCH₃ | " | |
| II-508 | " | " | " | " | " | OCOCH₃ | " | |
| II-509 | " | " | " | " | " | OSO₂CH₃ | " | |
| II-510 | " | " | " | " | " | OH | NH | |
| II-511 | 2,3-(CH₃)₂-4-SO₂CH₃ | " | " | " | " | OCOCH₃ | " | |
| II-512 | " | " | " | " | " | OSO₂CH₃ | " | |
| II-513 | " | " | " | " | " | OH | NCH₃ | |
| II-514 | " | " | " | " | " | OCOCH₃ | " | |
| II-515 | " | CH₃ | " | " | " | OH | NH | |
| II-516 | " | " | " | " | " | OCH₃ | " | |

TABLE 2-continued

Structural formula:

R⁴—C(R³)(R⁷)—C(X)(R⁵)—...—C(=O)—C(=O)—C₆H₄(R)ₙ with R² substituent

| Compound No. | (R)ₙ | R² | R³ | R⁴ | R⁵ | R⁷ | X | Physical constant [ ] m.p. °C. |
|---|---|---|---|---|---|---|---|---|
| II-517 | " | " | " | " | " | OCOCH₃ | " | |
| II-518 | " | " | " | " | " | OSO₂CH₃ | " | |
| II-519 | " | H | " | " | " | OH | " | |
| II-520 | " | " | " | " | " | OCH₃ | " | |
| II-521 | " | " | " | " | " | OCOCH₃ | " | |
| II-522 | " | " | " | " | " | OSO₂CH₃ | " | |
| II-523 | " | " | " | " | " | OH | NCH₃ | |
| II-524 | " | " | " | " | " | OCH₃ | " | |
| II-525 | " | " | " | " | " | OCOCH₃ | " | |
| II-526 | " | " | " | " | " | OSO₂CH₃ | " | |
| II-527 | " | CH₃ | " | " | " | OH | " | |
| II-528 | " | " | " | " | " | OCH₃ | " | |
| II-529 | " | " | " | " | " | OCOCH₃ | " | |
| II-530 | " | " | " | " | " | OSO₂CH₃ | " | |
| II-531 | " | H | " | " | CH₃ | OH | " | |
| II-532 | " | " | " | " | " | OCH₃ | " | |
| II-533 | " | " | " | " | " | OCOCH₃ | " | |
| II-534 | " | " | " | " | " | OSO₂CH₃ | " | |
| II-535 | " | " | " | " | " | OH | NC₂H₅ | |
| II-536 | " | " | " | " | " | OCH₃ | " | |
| II-537 | " | " | " | " | " | OCOCH₃ | " | |
| II-538 | " | " | " | " | " | OSO₂CH₃ | " | |
| II-539 | " | CH₃ | " | " | " | OH | " | |
| II-540 | " | " | " | " | " | OCH₃ | " | |
| II-541 | " | " | " | " | " | OCOCH₃ | " | |
| II-542 | " | " | " | " | " | OSO₂CH₃ | " | |
| II-543 | " | H | " | " | CH₃ | OH | " | |
| II-544 | " | " | " | " | " | OCH₃ | " | |
| II-545 | " | " | " | " | " | OCOCH₃ | " | |
| II-546 | " | " | " | " | " | OSO₂CH₃ | " | |
| II-547 | " | " | " | " | " | OH | NC₃H₇ⁱ | |
| II-548 | " | " | " | " | " | OCH₃ | " | |
| II-549 | " | " | " | " | " | OCOCH₃ | " | |
| II-550 | 2-CH₃-3-C₂H₅-4-SO₂CH₃ | " | " | " | " | OSO₂CH₃ | " | |
| II-551 | " | " | " | " | " | OH | NH | |
| II-552 | " | " | " | " | " | OCH₃ | " | |
| II-553 | " | " | " | " | " | OCOCH₃ | " | |
| II-554 | " | " | " | " | " | OSO₂CH₃ | " | |
| II-555 | " | " | " | " | " | OH | NCH₃ | |
| II-556 | " | " | " | " | " | OCH₃ | " | |
| II-557 | " | " | " | " | " | OCOCH₃ | " | |

TABLE 2-continued

Structural formula:

$$\begin{array}{c} R^2 \\ R^3 \\ R^4 \\ R^7 \end{array} R^5 \begin{array}{c} O \\ \\ X \end{array} \begin{array}{c} O \\ \\ \end{array} (R)_n$$

| Compound No. | (R)$_n$ | R$^2$ | R$^3$ | R$^4$ | R$^5$ | R$^7$ | X | Physical constant [ ] m.p. °C. |
|---|---|---|---|---|---|---|---|---|
| II-558 | " | " | " | " | " | OSO$_2$CH$_3$ | " | |
| II-559 | 2-CH$_3$-3-C$_3$H$_7$-i-4-SO$_2$CH$_3$ | " | " | " | " | OH | NH | |
| II-560 | " | " | " | " | " | OCH$_3$ | " | |
| II-561 | " | " | " | " | " | OCOCH$_3$ | " | |
| II-562 | " | " | " | " | " | OSO$_2$CH$_3$ | " | |
| II-563 | " | " | " | " | " | OH | NCH$_3$ | |
| II-564 | " | " | " | " | " | OCH$_3$ | " | |
| II-565 | " | " | " | " | " | OCOCH$_3$ | " | |
| II-566 | " | " | " | " | " | OSO$_2$CH$_3$ | " | |
| II-567 | 2-CH$_3$-3-CH$_2$OCH$_3$-4-SO$_2$CH$_3$ | " | " | " | " | OH | NH | |
| II-568 | " | " | " | " | " | OCH$_3$ | " | |
| II-569 | " | " | " | " | " | OCOCH$_3$ | " | |
| II-570 | " | " | " | " | " | OSO$_2$CH$_3$ | " | |
| II-571 | " | " | " | " | " | OH | NCH$_3$ | |
| II-572 | " | " | " | " | " | OCH$_3$ | " | |
| II-573 | " | " | " | " | " | OCOCH$_3$ | " | |
| II-574 | " | " | " | " | " | OSO$_2$CH$_3$ | " | |
| II-575 | 2-CH$_3$-3-CH$_2$CH$_2$OCH$_3$-4-SO$_2$CH$_3$ | " | " | " | " | OH | NH | |
| II-576 | " | " | " | " | " | OCH$_3$ | " | |
| II-577 | " | " | " | " | " | OCOCH$_3$ | " | |
| II-578 | " | " | " | " | " | OSO$_2$CH$_3$ | " | |
| II-579 | " | " | " | " | " | OH | NCH$_3$ | |
| II-580 | " | " | " | " | " | OCH$_3$ | " | |
| II-581 | " | " | " | " | " | OCOCH$_3$ | " | |
| II-582 | " | " | " | " | " | OSO$_2$CH$_3$ | " | |
| II-583 | 2-CH$_3$-3-CH$_2$CO$_2$CH$_3$-4-SO$_2$CH$_3$ | " | " | " | " | OH | NH | |
| II-584 | " | " | " | " | " | OCH$_3$ | " | |
| II-585 | " | " | " | " | " | OCOCH$_3$ | " | |
| II-586 | " | " | " | " | " | OSO$_2$CH$_3$ | " | |
| II-587 | " | " | " | " | " | OH | NCH$_3$ | |
| II-588 | " | " | " | " | " | OCH$_3$ | " | |
| II-589 | " | " | " | " | " | OCOCH$_3$ | " | |
| II-590 | " | " | " | " | " | OSO$_2$CH$_3$ | " | |
| II-591 | 2-CH$_3$-3-Cl-4-SO$_2$CH$_3$ | " | " | " | " | OH | NH | |
| II-592 | " | " | " | " | " | OCH$_3$ | " | |
| II-593 | " | " | " | " | " | OCOCH$_3$ | " | |
| II-594 | " | " | " | " | " | OSO$_2$CH$_3$ | " | |
| II-595 | " | " | " | " | " | OH | NCH$_3$ | |
| II-596 | " | " | " | " | " | OCH$_3$ | " | |
| II-597 | " | " | " | " | " | OCOCH$_3$ | " | |
| II-598 | " | " | " | " | " | OSO$_2$CH$_3$ | " | |

TABLE 2-continued

Structural formula

| Compound No. | (R)$_n$ | R$^2$ | R$^3$ | R$^4$ | R$^5$ | R$^7$ | X | Physical constant [ ] m.p. °C. |
|---|---|---|---|---|---|---|---|---|
| II-599 | " | " | " | " | " | OH | NC$_2$H$_5$ | |
| II-600 | " | " | " | " | " | OCH$_3$ | " | |
| II-601 | " | " | " | " | " | OCOCH$_3$ | " | |
| II-602 | " | " | " | " | " | OSO$_2$CH$_3$ | " | |
| II-603 | " | " | " | " | " | OH | NC$_3$H$_7^i$ | |
| II-604 | " | " | " | " | " | OCH$_3$ | " | |
| II-605 | " | " | " | " | " | OCOCH$_3$ | " | |
| II-606 | " | " | " | " | " | OSO$_2$CH$_3$ | " | |
| II-607 | 2-CH$_3$-3-CO$_2$CH$_3$-4-SO$_2$CH$_3$ | " | " | " | " | OH | NH | |
| II-608 | " | " | " | " | " | OCH$_3$ | " | |
| II-609 | " | " | " | " | " | OCOCH$_3$ | " | |
| II-610 | " | " | " | " | " | OSO$_2$CH$_3$ | " | |
| II-611 | " | " | " | " | " | OH | NCH$_3$ | |
| II-612 | " | " | " | " | " | OCH$_3$ | " | |
| II-613 | " | " | " | " | " | OCOCH$_3$ | " | |
| II-614 | " | " | " | " | " | OSO$_2$CH$_3$ | " | |
| II-615 | " | " | " | " | " | OH | NC$_2$H$_5$ | |
| II-616 | " | " | " | " | " | OCH$_3$ | " | |
| II-617 | " | " | " | " | " | OCOCH$_3$ | " | |
| II-618 | " | " | " | " | " | OSO$_2$CH$_3$ | " | |
| II-619 | " | " | " | " | " | OH | NC$_3$H$_7^i$ | |
| II-620 | " | " | " | " | " | OCH$_3$ | " | |
| II-621 | " | " | " | " | " | OCOCH$_3$ | " | |
| II-622 | " | " | " | " | " | OSO$_2$CH$_3$ | " | |
| II-623 | 2-CH$_3$-3-OCH$_3$-4-SO$_2$CH$_3$ | " | " | " | " | OH | NH | |
| II-624 | " | " | " | " | " | OCH$_3$ | " | |
| II-625 | " | " | " | " | " | OCOCH$_3$ | " | |
| II-626 | " | " | " | " | " | OSO$_2$CH$_3$ | " | |
| II-627 | " | CH$_3$ | " | " | " | OH | NCH$_3$ | |
| II-628 | " | " | " | " | CH$_3$ | OCH$_3$ | " | |
| II-629 | " | " | " | " | " | OCOCH$_3$ | " | |
| II-630 | " | " | " | " | " | OSO$_2$CH$_3$ | " | |
| II-631 | " | H | " | " | " | OH | " | |
| II-632 | " | " | " | " | H | OCH$_3$ | " | |
| II-633 | " | " | " | " | " | OCOCH$_3$ | " | |
| II-634 | " | " | " | " | " | OSO$_2$CH$_3$ | " | |
| II-635 | " | " | " | " | " | OH | NCH$_3$ | |
| II-636 | " | " | " | " | " | OCH$_3$ | " | |
| II-637 | " | " | " | " | " | OCOCH$_3$ | " | |
| II-638 | " | CH$_3$ | " | " | " | OSO$_2$CH$_3$ | " | powder*27 |
| II-639 | " | " | " | " | " | OH | " | powder*28 |

TABLE 2-continued

Structural formula:

$$R^2, R^3, R^4, R^5, R^7 \text{ substituents on structure with } (R)_n \text{ phenyl}$$

| Compound No. | (R)$_n$ | R$^2$ | R$^3$ | R$^4$ | R$^5$ | R$^7$ | X | Physical constant [ ] m.p. °C. |
|---|---|---|---|---|---|---|---|---|
| II-640 | " | " | " | " | " | OCH$_3$ | " | |
| II-641 | " | " | " | " | " | OCOCH$_3$ | " | |
| II-642 | " | " | " | " | " | OSO$_2$CH$_3$ | " | |
| II-643 | " | H | " | " | " | OH | " | |
| II-644 | " | " | " | " | " | OCH$_3$ | " | |
| II-645 | " | " | " | " | " | OCOCH$_3$ | " | |
| II-646 | " | " | " | " | " | OSO$_2$CH$_3$ | " | |
| II-647 | " | " | " | " | CH$_3$ | OH | NC$_2$H$_5$ | |
| II-648 | " | " | " | " | " | OCH$_3$ | " | |
| II-649 | " | " | " | " | " | OCOCH$_3$ | " | |
| II-650 | " | " | " | " | " | OSO$_2$CH$_3$ | " | |
| II-651 | " | CH$_3$ | " | " | H | OH | " | |
| II-652 | " | " | " | " | " | OCH$_3$ | " | |
| II-653 | " | " | " | " | " | OCOCH$_3$ | " | |
| II-654 | " | " | " | " | " | OSO$_2$CH$_3$ | " | |
| II-655 | " | H | " | " | CH$_3$ | OH | " | |
| II-656 | " | " | " | " | " | OCH$_3$ | " | |
| II-657 | " | " | " | " | " | OCOCH$_3$ | " | |
| II-658 | " | " | " | " | " | OSO$_2$CH$_3$ | " | |
| II-659 | " | " | " | " | H | OH | NC$_3$H$_7^i$ | |
| II-660 | " | " | " | " | " | OCH$_3$ | " | |
| II-661 | " | " | " | " | " | OCOCH$_3$ | " | |
| II-662 | " | " | " | " | " | OSO$_2$CH$_3$ | " | |
| II-663 | 2-CH$_3$-3-OC$_4$H$_9^n$-4-SO$_2$CH$_3$ | " | " | " | " | OH | NH | |
| II-664 | " | " | " | " | " | OCH$_3$ | " | |
| II-665 | " | " | " | " | " | OCOCH$_3$ | " | |
| II-666 | " | " | " | " | " | OSO$_2$CH$_3$ | " | |
| II-667 | " | " | " | " | " | OH | NCH$_3$ | |
| II-668 | " | " | " | " | " | OCH$_3$ | " | |
| II-669 | " | " | " | " | " | OCOCH$_3$ | " | |
| II-670 | " | " | " | " | " | OSO$_2$CH$_3$ | " | |
| II-671 | " | " | " | " | " | OH | NC$_2$H$_5$ | |
| II-672 | " | " | " | " | " | OCH$_3$ | " | |
| II-673 | " | " | " | " | " | OCOCH$_3$ | " | |
| II-674 | " | " | " | " | " | OSO$_2$CH$_3$ | " | |
| II-675 | " | " | " | " | " | OH | NC$_3$H$_7^i$ | |
| II-676 | " | " | " | " | " | OCH$_3$ | " | |
| II-677 | " | " | " | " | " | OCOCH$_3$ | " | |
| II-678 | " | " | " | " | " | OSO$_2$CH$_3$ | " | |
| II-679 | " | " | " | " | " | OH | NH | |
| II-680 | 2-CH$_3$-3-OCH$_2$CH=CH$_2$-4-SO$_2$CH$_3$ | " | " | " | " | OCH$_3$ | " | |

TABLE 2-continued

Structural formula:

$$R^4 \underset{R^7}{\overset{R^3}{\diagup}} R^5 \quad \text{(backbone with } R^2, \text{ carbonyls, } X, \text{ and phenyl-}(R)_n\text{)}$$

| Compound No. | $(R)_n$ | $R^2$ | $R^3$ | $R^4$ | $R^5$ | $R^7$ | X | Physical constant [ ] m.p. °C. |
|---|---|---|---|---|---|---|---|---|
| II-681 | " | " | " | " | " | OCOCH$_3$ | " | |
| II-682 | " | " | " | " | " | OSO$_2$CH$_3$ | " | |
| II-683 | " | " | " | " | " | OH | NCH$_3$ | |
| II-684 | " | " | " | " | " | OCH$_3$ | " | |
| II-685 | " | " | " | " | " | OCOCH$_3$ | " | |
| II-686 | " | " | " | " | " | OSO$_2$CH$_3$ | " | |
| II-687 | " | " | " | " | " | OH | NC$_2$H$_5$ | |
| II-688 | " | " | " | " | " | OCH$_3$ | " | |
| II-689 | " | " | " | " | " | OCOCH$_3$ | " | |
| II-690 | " | " | " | " | " | OSO$_2$CH$_3$ | " | |
| II-691 | " | " | " | " | " | OH | NC$_3$H$_7^i$ | |
| II-692 | " | " | " | " | " | OCH$_3$ | " | |
| II-693 | " | " | " | " | " | OCOCH$_3$ | " | |
| II-694 | " | " | " | " | " | OSO$_2$CH$_3$ | " | |
| II-695 | 2-CH$_3$-3-OCH$_2$C≡CH-4-SO$_2$CH$_3$ | " | " | " | " | OH | NH | |
| II-696 | " | " | " | " | " | OCH$_3$ | " | |
| II-697 | " | " | " | " | " | OCOCH$_3$ | " | |
| II-698 | " | " | " | " | " | OSO$_2$CH$_3$ | " | |
| II-699 | " | " | " | " | " | OH | NC$_2$H$_5$ | |
| II-700 | " | " | " | " | " | OCH$_3$ | " | |
| II-701 | " | " | " | " | " | OCOCH$_3$ | " | |
| II-702 | " | " | " | " | " | OSO$_2$CH$_3$ | " | |
| II-703 | " | " | " | " | " | OH | NC$_3$H$_7^i$ | |
| II-704 | " | " | " | " | " | OCH$_3$ | " | |
| II-705 | " | " | " | " | " | OCOCH$_3$ | " | |
| II-706 | " | " | " | " | " | OSO$_2$CH$_3$ | " | |
| II-707 | 2-CH$_3$-3-OCH$_2$CH$_2$OCH$_3$-4-SO$_2$CH$_3$ | " | " | " | " | OH | NH | |
| II-708 | " | " | " | " | " | OCH$_3$ | " | |
| II-709 | " | " | " | " | " | OCOCH$_3$ | " | |
| II-710 | " | " | " | " | " | OSO$_2$CH$_3$ | " | |
| II-711 | 2-CH$_3$-3-OCH$_2$CH$_2$OCH$_3$-4-SO$_2$CH$_3$ | CH$_3$ | H | H | H | OH | NH | |
| II-712 | " | " | " | " | " | OCH$_3$ | " | |
| II-713 | " | " | " | " | " | OCOCH$_3$ | " | |
| II-714 | " | " | " | " | " | OSO$_2$CH$_3$ | " | |
| II-715 | " | H | " | " | CH$_3$ | OH | " | |
| II-716 | " | " | " | " | " | OCH$_3$ | " | |
| II-717 | " | " | " | " | " | OCOCH$_3$ | " | |
| II-718 | " | " | " | " | " | OSO$_2$CH$_3$ | " | |
| II-719 | " | " | " | " | H | OH | NCH$_3$ | powder*29 |
| II-720 | " | " | " | " | " | OCH$_3$ | " | |

TABLE 2-continued

Structural formula:

$$R^4 \underset{R^7}{\overset{R^3}{\diagdown}} R^5$$ ... with phenyl ring bearing $(R)_n$, and groups $R^2$, $R^3$, $R^4$, $R^5$, $R^7$, X on the chain with two C=O groups.

| Compound No. | (R)$_n$ | R$^2$ | R$^3$ | R$^4$ | R$^5$ | R$^7$ | X | Physical constant [ ] m.p. °C. |
|---|---|---|---|---|---|---|---|---|
| II-721 | | | | | | OCOCH$_3$ | | |
| II-722 | " | CH$_3$ | " | " | " | OSO$_2$CH$_3$ | " | |
| II-723 | " | " | " | " | " | OH | " | |
| II-724 | " | " | " | " | " | OCH$_3$ | " | |
| II-725 | " | " | " | " | " | OCOCH$_3$ | " | |
| II-726 | " | H | " | " | " | OSO$_2$CH$_3$ | " | |
| II-727 | " | " | " | " | " | OH | " | |
| II-728 | " | " | " | " | " | OCH$_3$ | " | |
| II-729 | " | " | " | " | CH$_3$ | OCOCH$_3$ | " | |
| II-730 | " | " | " | " | " | OSO$_2$CH$_3$ | " | |
| II-731 | " | " | " | " | " | OH | NC$_2$H$_5$ | |
| II-732 | " | " | " | " | " | OCH$_3$ | " | |
| II-733 | " | " | " | " | H | OCOCH$_3$ | " | |
| II-734 | " | CH$_3$ | " | " | " | OSO$_2$CH$_3$ | " | |
| II-735 | " | " | " | " | " | OH | " | |
| II-736 | " | " | " | " | " | OCH$_3$ | " | |
| II-737 | " | " | " | " | CH$_3$ | OCOCH$_3$ | " | |
| II-738 | " | " | " | " | " | OSO$_2$CH$_3$ | " | |
| II-739 | " | H | " | " | " | OH | " | |
| II-740 | " | " | " | " | " | OCH$_3$ | " | |
| II-741 | " | " | " | " | " | OCOCH$_3$ | " | |
| II-742 | " | " | " | " | " | OSO$_2$CH$_3$ | " | |
| II-743 | " | " | " | " | " | OH | NC$_3$H$_7^i$ | |
| II-744 | " | " | " | " | " | OCH$_3$ | " | |
| II-745 | " | " | " | " | H | OCOCH$_3$ | " | |
| II-746 | " | " | " | " | " | OSO$_2$CH$_3$ | " | |
| II-747 | 2-CH$_3$-3-OCH$_2$CH$_2$SCH$_3$-4-SO$_2$CH$_3$ | " | " | " | " | OH | NH | |
| II-748 | " | " | " | " | " | OCH$_3$ | " | |
| II-749 | " | " | " | " | " | OCOCH$_3$ | " | |
| II-750 | " | " | " | " | " | OSO$_2$CH$_3$ | " | |
| II-751 | " | " | " | " | " | OH | NCH$_3$ | |
| II-752 | " | " | " | " | " | OCH$_3$ | " | |
| II-753 | " | " | " | " | " | OCOCH$_3$ | " | |
| II-754 | " | " | " | " | " | OSO$_2$CH$_3$ | " | |
| II-755 | " | " | " | " | " | OH | NC$_2$H$_5$ | |
| II-756 | " | " | " | " | " | OCH$_3$ | " | |
| II-757 | " | " | " | " | " | OCOCH$_3$ | " | |
| II-758 | " | " | " | " | " | OSO$_2$CH$_3$ | " | |
| II-759 | " | " | " | " | " | OH | NC$_3$H$_7^i$ | |
| II-760 | " | " | " | " | " | OCH$_3$ | " | |
| II-761 | " | " | " | " | " | OCOCH$_3$ | " | |

TABLE 2-continued

Structural formula:

$R^2, R^3, R^4, R^5, R^7$ substituents on a cyclohexanedione ring with X, and a benzoyl group with $(R)_n$

| Compound No. | (R)$_n$ | R$^2$ | R$^3$ | R$^4$ | R$^5$ | R$^7$ | X | Physical constant [ ] m.p. °C. |
|---|---|---|---|---|---|---|---|---|
| II-762 | " | " | " | " | " | OSO$_2$CH$_3$ | " | |
| II-763 | 2-CH$_3$-3-OC$_3$H$_7$-i-4-SO$_2$CH$_3$ | " | " | " | " | OH | NH | |
| II-764 | " | " | " | " | " | OCH$_3$ | " | |
| II-765 | " | " | " | " | " | OCOCH$_3$ | " | |
| II-766 | " | " | " | " | " | OSO$_2$CH$_3$ | " | |
| II-767 | " | " | " | " | " | OH | NCH$_3$ | |
| II-768 | " | " | " | " | " | OCH$_3$ | " | |
| II-769 | " | " | " | " | " | OCOCH$_3$ | " | |
| II-770 | " | " | " | " | " | OSO$_2$CH$_3$ | " | |
| II-771 | 2-CH$_3$-3-OCH$_2$CH=CHCl-4-SO$_2$CH$_3$ | " | " | " | " | OH | NH | |
| II-772 | " | " | " | " | " | OCH$_3$ | " | |
| II-773 | " | " | " | " | " | OCOCH$_3$ | " | |
| II-774 | " | " | " | " | " | OSO$_2$CH$_3$ | " | |
| II-775 | " | " | " | " | " | OH | NCH$_3$ | |
| II-776 | " | " | " | " | " | OCH$_3$ | " | |
| II-777 | " | " | " | " | " | OCOCH$_3$ | " | |
| II-778 | " | " | " | " | " | OSO$_2$CH$_3$ | " | |
| II-779 | 2-CH$_3$-3-OCH$_2$CH(CH$_3$)OCH$_3$-4-SO$_2$CH$_3$ | " | " | " | " | OH | NH | |
| II-780 | " | " | " | " | " | OCH$_3$ | " | |
| II-781 | " | " | " | " | " | OCOCH$_3$ | " | |
| II-782 | " | " | " | " | " | OSO$_2$CH$_3$ | " | |
| II-783 | " | " | " | " | " | OH | NCH$_3$ | |
| II-784 | " | " | " | " | " | OCH$_3$ | " | |
| II-785 | " | " | " | " | " | OCOCH$_3$ | " | |
| II-786 | " | " | " | " | " | OSO$_2$CH$_3$ | " | |
| II-787 | 2-CH$_3$-3-SCH$_3$-4-SO$_2$CH$_3$ | " | " | " | " | OH | NH | |
| II-788 | " | " | " | " | " | OCH$_3$ | " | |
| II-789 | " | " | " | " | " | OCOCH$_3$ | " | |
| II-790 | " | " | " | " | " | OSO$_2$CH$_3$ | " | |
| II-791 | " | " | " | " | " | OH | NCH$_3$ | |
| II-792 | " | " | " | " | " | OCH$_3$ | " | |
| II-793 | " | " | " | " | " | OCOCH$_3$ | " | |
| II-794 | " | " | " | " | " | OSO$_2$CH$_3$ | " | |
| II-795 | 2-CH$_2$CH=CH$_2$-3-OCH$_3$-4-SO$_2$CH$_3$ | " | " | " | " | OH | NH | |
| II-796 | " | " | " | " | " | OCH$_3$ | " | |

TABLE 2-continued

Structural formula

| Compound No. | (R)$_n$ | R$^2$ | R$^3$ | R$^4$ | R$^5$ | R$^7$ | X | Physical constant [ ] m.p. °C. |
|---|---|---|---|---|---|---|---|---|
| II-797 | " | " | " | " | " | OCOCH$_3$ | " | |
| II-798 | " | " | " | " | " | OSO$_2$CH$_3$ | " | |
| II-799 | " | " | " | " | " | OH | NCH$_3$ | |
| II-800 | " | " | " | " | " | OCH$_3$ | " | powder |
| II-801 | " | " | " | " | " | OCOCH$_3$ | " | |
| II-802 | " | " | " | " | " | OSO$_2$CH$_3$ | " | |
| II-803 | 3-NO$_2$-4-SCH$_3$ | " | " | " | " | OH | " | |
| II-804 | " | " | " | " | " | OCH$_3$ | " | |
| II-805 | 3-OCH$_2$CH$_2$OCH$_3$-4-SO$_2$CH$_3$ | " | " | " | " | OH | " | |
| II-806 | " | " | " | " | " | OCH$_3$ | " | powder*30 |
| II-807 | 2-Cl-3-OCH$_2$CH$_2$OCH$_3$-4-SO$_2$CH$_3$ | " | " | " | " | OH | O | |
| II-808 | " | " | " | " | " | OCH$_3$ | " | |
| II-809 | " | " | " | " | " | OCOCH$_3$ | " | |
| II-810 | " | " | " | " | " | OSO$_2$CH$_3$ | " | |
| II-811 | 2-Cl-3-CO$_2$CH$_3$-4-SO$_2$CH$_3$ | " | " | " | " | OH | " | |
| II-812 | " | " | " | " | " | OCH$_3$ | " | |
| II-813 | " | " | " | " | " | OCOCH$_3$ | " | |
| II-814 | " | " | " | " | " | OSO$_2$CH$_3$ | " | |
| II-815 | 2-CH$_3$-3-OCH$_2$CH$_2$OCH$_3$-4-SO$_2$CH$_3$ | " | " | " | " | OH | " | |
| II-816 | " | " | " | " | " | OCH$_3$ | " | |
| II-817 | " | " | " | " | " | OCOCH$_3$ | " | |
| II-818 | " | " | " | " | " | OSO$_2$CH$_3$ | " | |
| II-819 | 2-CH$_3$-3-CO$_2$CH$_3$-4-SO$_2$CH$_3$ | " | " | " | " | OH | " | |
| II-820 | " | " | " | " | " | OCH$_3$ | " | |
| II-821 | " | " | " | " | " | OCOCH$_3$ | " | |
| II-822 | " | " | " | " | " | OSO$_2$CH$_3$ | " | |
| II-823 | " | " | " | " | " | OH | " | |
| II-824 | " | " | " | " | " | OCH$_3$ | " | |
| II-825 | " | " | " | " | " | OCOCH$_3$ | " | |
| II-826 | " | " | " | " | " | OSO$_2$CH$_3$ | " | |
| II-827 | " | " | " | " | " | OH | " | |
| II-828 | " | " | " | " | " | OCH$_3$ | " | |
| II-829 | " | " | " | " | " | OCOCH$_3$ | " | |
| II-830 | " | " | " | " | " | OSO$_2$CH$_3$ | " | |
| II-831 | 2-NO$_2$-4-Cl | " | " | " | " | OH | " | |
| II-832 | " | " | " | " | " | OCH$_3$ | " | |
| II-833 | " | " | " | " | " | OCOCH$_3$ | S | |
| II-834 | " | " | " | " | " | OSO$_2$CH$_3$ | " | |
| II-835 | 2-NO$_2$-4-CF$_3$ | " | " | " | " | OH | " | |
| II-836 | " | " | " | " | " | OCH$_3$ | " | |
| II-837 | " | " | " | " | " | OCOCH$_3$ | " | |

TABLE 2-continued

Structural formula:

$$R^4\underset{R^7}{\overset{R^3}{>}}R^5 \quad \text{(with cyclohexanedione bearing benzoyl group with }(R)_n\text{ and X)}$$

| Compound No. | (R)ₙ | R² | R³ | R⁴ | R⁵ | R⁷ | X | Physical constant [ ] m.p. °C. |
|---|---|---|---|---|---|---|---|---|
| II-838 | " | " | " | " | " | OSO₂CH₃ | " | |
| II-839 | 2-NO₂-4-SO₂CH₃ | " | " | " | " | OH | " | |
| II-840 | " | " | " | " | " | OCH₃ | " | |
| II-841 | " | " | " | " | " | OCOCH₃ | " | |
| II-842 | " | " | " | " | " | OSO₂CH₃ | " | |
| II-843 | 2-Cl-4-SO₂CH₃ | " | " | " | " | OH | " | |
| II-844 | " | " | " | " | " | OCH₃ | " | |
| II-845 | " | " | " | " | " | OCOCH₃ | " | |
| II-846 | " | " | " | " | " | OSO₂CH₃ | " | |
| II-847 | 2,3-Cl₂-4-SO₂CH₃ | " | " | " | " | OH | " | |
| II-848 | " | " | " | " | " | OCH₃ | " | |
| II-849 | " | " | " | " | " | OCOCH₃ | " | |
| II-850 | " | " | " | " | " | OSO₂CH₃ | " | |
| II-851 | 2-Cl-3-CH₃-4-SO₂CH₃ | " | " | " | " | OH | " | |
| II-852 | " | " | " | " | " | OCH₃ | " | |
| II-853 | " | " | " | " | " | OCOCH₃ | " | |
| II-854 | " | " | " | " | " | OSO₂CH₃ | " | |
| II-855 | 2-Cl-3-CO₂CH₃-4-SO₂CH₃ | " | " | " | " | OH | " | |
| II-856 | " | " | " | " | " | OCH₃ | " | |
| II-857 | " | " | " | " | " | OCOCH₃ | " | |
| II-858 | " | " | " | " | " | OSO₂CH₃ | " | |
| II-859 | 2-Cl-3-OCH₃-4-SO₂CH₃ | " | " | " | " | OH | " | |
| II-860 | " | " | " | " | " | OCH₃ | " | |
| II-861 | " | " | " | " | " | OCOCH₃ | " | |
| II-862 | " | " | " | " | " | OSO₂CH₃ | " | |
| II-863 | 2-Cl-3-OCH₂CH₂OCH₃-4-SO₂CH₃ | " | " | " | " | OH | " | |
| II-864 | " | " | " | " | " | OCH₃ | " | |
| II-865 | " | " | " | " | " | OCOCH₃ | " | |
| II-866 | " | " | " | " | " | OSO₂CH₃ | " | |
| II-867 | 2,3-(CH₃)₂-4-SO₂CH₃ | " | " | " | " | OH | " | |
| II-868 | " | " | " | " | " | OCH₃ | " | |
| II-869 | " | " | " | " | " | OCOCH₃ | " | |
| II-870 | " | " | " | " | " | OSO₂CH₃ | " | |
| II-871 | 2-CH₃-3-Cl-4-SO₂CH₃ | " | " | " | " | OH | " | |
| II-872 | " | " | " | " | " | OCH₃ | " | |
| II-873 | " | " | " | " | " | OCOCH₃ | " | |
| II-874 | " | " | " | " | " | OSO₂CH₃ | " | |
| II-875 | 2-CH₃-3-CO₂CH₃-4-SO₂CH₃ | " | " | " | " | OH | " | |
| II-876 | " | " | " | " | " | OCH₃ | " | |
| II-877 | " | " | " | " | " | OCOCH₃ | " | |
| II-878 | " | " | " | " | " | OSO₂CH₃ | " | |

TABLE 2-continued

Structural formula:

R², R³, R⁴, R⁵, R⁷ attached to central structure with C=O groups and X, connected to phenyl ring with (R)ₙ substituents.

| Compound No. | (R)ₙ | R² | R³ | R⁴ | R⁵ | R⁷ | X | Physical constant [ ] m.p. °C. |
|---|---|---|---|---|---|---|---|---|
| II-879 | 2-CH₃-3-OCH₃-4-SO₂CH₃ | | | | | OH | O | |
| II-880 | " | " | " | " | " | OCH₃ | " | |
| II-881 | " | " | " | " | " | OCOCH₃ | " | |
| II-882 | " | " | " | " | " | OSO₂CH₃ | " | |
| II-883 | 2-CH₃-3-OCH₂CH₂OCH₃-4-SO₂CH₃ | " | " | " | " | OH | " | |
| II-884 | " | " | " | " | " | OCH₃ | " | |
| II-885 | " | " | " | " | " | OCOCH₃ | " | |
| II-886 | " | " | " | " | " | OSO₂CH₃ | " | |
| II-887 | " | CH₃ | " | " | " | OH | " | |
| II-888 | " | " | " | " | " | OCH₃ | " | |
| II-889 | " | " | " | " | " | OCOCH₃ | " | |
| II-890 | " | " | " | " | " | OSO₂CH₃ | " | |
| II-891 | " | H | " | " | CH₃ | OH | " | |
| II-892 | " | " | " | " | " | OCH₃ | " | |
| II-893 | " | " | " | " | " | OCOCH₃ | " | |
| II-894 | " | " | " | " | " | OSO₂CH₃ | " | |

¹H-NMR(CDCl₃) δ;ppm

*²2.66(m, 2H), 3.63(m, 2H), 3.76(m, 2H), 3.82(m, 1H), 4.73(m, 2H), 6.89(m, 2H), 7.31(m, 2H), 7.33(m, 1H), 7.66(m, 1H), 8.12(m, 1H)
*¹⁰2.60(m, 2H), 3.24(s, 3H), 3.35(s, 3H), 3.48(m, 2H), 3.70(m, 2H), 3.65(m, 3H), 7.46(d, 1H), 7.92(d, 1H), 8.44(s, 1H)
*¹¹2.60(s, 3H), 2.62(m, 2H), 3.22(s, 3H), 3.65(m, 3H), 7.26(m, 1H), 7.47(m, 1H), 7.93(m, 1H)
*¹²2.70(m, 2H), 3.23(s, 3H), 3.33(s, 3H), 3.25(s, 3H), 3.60(bs, 6H), 3.50(m, 2H), 3.57(m, 2H), 3.69(m, 1H), 3.77(m, 2H), 5.20(m, 2H), 7.34(m, 1H), 8.11(m, 1H)
*¹³2.65(m, 2H), 3.20(s, 3H), 3.23(s, 3H), 3.25(s, 3H), 3.32(s, 3H), 3.50(m, 2H), 3.60(m, 2H), 3.72(m, 1H), 4.00(s, 3H), 7.45(m, 1H), 8.00(m, 1H)
*¹⁴2.56(m, 2H), 2.63(bs, 3H), 3.23(bs, 3H), 3.67(m, 3H), 7.26(m, 1H), 7.49(m, 1H), 7.93(m, 1H)
*¹⁵1.23(m, 3H), 2.66(m, 2H), 2.79(m, 2H), 3.20(s, 3H), 3.59(m, 2H), 4.03(s, 3H), 7.07(m, 1H), 7.87(m, 1H)
*¹⁶1.29(m, 3H), 2.53(m, 2H), 3.19(s, 3H), 3.30(s, 3H), 3.40(m, 2H), 3.79(m, 1H), 4.05(s, 3H) 7.13(m, 1H), 7.89(m, 1H)
*¹⁷2.53(m, 2H), 3.23(s, 3H), 3.57(m, 3H), 4.01(s, 3H), 4.69(m, 2H), 6.84(m, 2H), 7.13(m, 2H), 7.26(m, 1H), 7.84(m, 1H)
*¹⁸1.00(m, 3H), 1.54(m, 2H), 1.88(m, 2H), 2.70(m, 2H), 3.24(s, 3H), 3.27(s, 3H), 3.50(m, 2H), 3.71(m, 1H), 4.26(m, 2H), 7.13(m, 1H), 7.91(m, 1H)
*¹⁹2.70(m, 2H), 3.21(s, 3H), 3.25(m, 3H), 3.44(s, 3H), 3.48(s, 3H), 3.72(m, 1H), 4.76(m, 2H), 5.40(m, 2H), 6.20(m, 1H), 7.15(m, 1H), 7.93(m, 1H)
*²⁰2.65(m, 3H), 3.23(s, 3H), 3.30(s, 3H), 3.43(s, 3H), 3.50(m, 2H), 3.74(m, 1H), 4.89(m, 2H), 7.20(m, 1H), 7.94(m, 1H)
*²¹2.65(m, 2H), 3.24(bs, 3H), 3.33(s, 3H), 3.49(s, 3H), 3.70(m, 3H), 3.46(m, 1H), 4.42(m, 2H), 7.14(m, 1H), 7.93(m, 1H)
*²²2.74(m, 2H), 3.23(s, 3H), 3.28(s, 3H), 3.33(s, 3H), 3.46(s, 3H), 3.70(m, 1H), 3.83(m, 2H), 4.31(m, 2H), 7.14(m, 1H), 7.93(m, 1H)
*²³2.05(m, 3H), 2.70(m, 2H), 3.31(s, 3H), 3.23(s, 3H), 3.48(s, 3H), 3.48(s, 3H), 3.85(m, 3H), 4.20(m, 1H), 4.42(m, 2H), 7.13(m, 1H), 7.95(m, 1H)
*²⁴1.26(m, 3H), 2.46(m, 2H), 3.23(s, 3H), 3.30(m, 7H), 3.46(s, 3H), 3.84(m, 2H), 4.43(m, 2H), 7.15(m, 1H), 7.94(m, 1H)
*²⁵1.30(m, 3H), 2.70(m, 2H), 3.30(m, 6H), 3.48(bs, 4H), 3.74(m, 2H), 3.83(s, 3H), 4.04(m, 2H), 4.41(m, 2H), 7.15(s, 1H), 7.95(m, 1H)
*²⁶2.20(s, 3H), 2.64(m, 2H), 3.00(m, 2H), 3.20(s, 3H), 3.25(s, 3H), 3.30(s, 3H), 3.35(m, 3H), 3.50(m, 2H), 3.83(m, 1H), 4.40(m, 2H), 7.15(m, 1H), 7.94(m, 1H)
*²⁷2.21(bs, 3H), 2.68(m, 2H), 3.20(s, 3H), 3.23(s, 3H), 3.57(m, 3H), 3.68(m, 3H), 3.95(s, 3H), 7.04(m, 1H), 7.88(m, 1H)
*²⁸2.23(bs, 3H), 2.65(m, 2H), 3.20(s, 6H), 3.23(s, 6H), 3.42(bs, 3H), 3.52(m, 2H), 3.71(m, 1H), 3.97(s, 3H), 7.05(m, 1H), 7.84(m, 1H)
*²⁹2.25(m, 3H), 2.65(m, 2H), 3.20(s, 3H), 3.25(s, 3H), 3.35(s, 3H), 3.48(s, 3H), 3.53(m, 1H), 3.70(m, 2H), 3.80(m, 2H), 4.24(m, 2H), 7.04(m, 1H), 7.84(m, 1H)
*³⁰2.70(m, 2H), 3.22(s, 3H), 3.30(s, 3H), 3.36(s, 3H), 3.45(s, 3H), 3.53(m, 2H), 3.70(m, 1H), 3.80(m, 2H), 4.28(m, 2H), 7.10(m, 1H), 7.17(d, 1H), 7.96(d, 1H)

TABLE 3

Structural formula

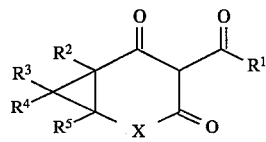

| Compound No. | R¹ | R² | R³ | R⁴ | R⁵ | X | Physical constant [ ] m.p. °C. |
|---|---|---|---|---|---|---|---|
| III-1 | 5-Cl-2-pyridyl | H | H | H | H | O | |
| III-2 | " | " | " | " | CH₃ | " | |
| III-3 | 5-CF₃-2-pyridyl | " | " | " | H | " | |
| III-4 | " | " | " | " | CH₃ | " | |
| III-5 | 5-SCH₃-2-pyridyl | " | " | " | H | " | |
| III-6 | " | " | " | " | CH₃ | " | |
| III-7 | 5-SO₂CH₃-2-pyridyl | " | " | " | H | " | |
| III-8 | " | " | " | " | CH₃ | " | |
| III-9 | 5-Cl-2-pyridyl | " | " | " | H | NH | |
| III-10 | " | CH₃ | " | " | " | " | |
| III-11 | 5-CF₃-2-pyridyl | H | " | " | " | " | |
| III-12 | " | CH₃ | " | " | " | " | |
| III-13 | 5-SCH₃-2-pyridyl | H | " | " | " | " | |
| III-14 | 5-SCH₃-2-pyridyl | CH₃ | H | H | H | NH | |
| III-15 | 5-SO₂CH₃-2-pyridyl | H | " | " | " | " | |
| III-16 | " | CH₃ | " | " | " | " | |
| III-17 | 5-Cl-2-pyridyl | H | " | " | " | NCH₃ | |
| III-18 | " | CH₃ | " | " | " | " | |
| III-19 | 5-CF₃-2-pyridyl | H | " | " | " | " | |
| III-20 | " | CH₃ | " | " | " | " | |
| III-21 | 5-SCH₃-2-pyridyl | H | " | " | " | " | |
| III-22 | " | CH₃ | " | " | " | " | |
| III-23 | 5-SO₂CH₃-2-pyridyl | H | " | " | " | " | |
| III-24 | " | CH₃ | " | " | " | " | |
| III-25 | 5-Cl-2-pyridyl | H | " | " | " | S | |
| III-26 | 5-SO₂CH₃-2-pyridyl | " | " | " | " | " | |
| III-27 | 2-CH₃-6-Cl-3-pyridyl | " | " | " | " | O | |
| III-28 | " | " | " | " | CH₃ | " | |
| III-29 | 2-CH₃-6-CF₃-3-pyridyl | " | " | " | H | " | |
| III-30 | 2-CH₃-6-CF₃-3-pyridyl | H | H | H | CH₃ | O | |
| III-31 | 2-CH₃-6-SCH₃-3-pyridyl | " | " | " | H | " | |
| III-32 | " | " | " | " | CH₃ | " | |
| III-33 | 2-CH₃-6-SOCH₃-3-pyridyl | " | " | " | H | " | |
| III-34 | " | " | " | " | CH₃ | " | |
| III-35 | 2-CH₃-6-SO₂CH₃-3-pyridyl | " | " | " | H | " | |
| III-36 | " | " | " | " | CH₃ | " | |
| III-37 | 2-CH₃-6-Cl-3-pyridyl | " | " | " | H | NH | |
| III-38 | " | CH₃ | " | " | " | " | |
| III-39 | 2-CH₃-6-CF₃-3-pyridyl | H | " | " | " | " | |
| III-40 | " | CH₃ | " | " | " | " | |
| III-41 | 2-CH₃-6-SCH₃-3-pyridyl | H | " | " | " | " | |
| III-42 | " | CH₃ | " | " | " | " | |
| III-43 | 2-CH₃-6-SOCH₃-3-pyridyl | H | " | " | " | " | |
| III-44 | " | CH₃ | " | " | " | " | |
| III-45 | 2-CH₃-6-SO₂CH₃-3-pyridyl | H | " | " | " | " | |
| III-46 | 2-CH₃-6-SO₂CH₃-3-pyridyl | CH₃ | H | H | H | NH | |
| III-47 | 2-CH₃-6-Cl-3-pyridyl | H | " | " | " | NCH₃ | [147–9] |
| III-48 | " | CH₃ | " | " | " | " | |
| III-49 | 2-CH₃-6-CF₃-3-pyridyl | H | " | " | " | " | |
| III-50 | " | CH₃ | " | " | " | " | |
| III-51 | 2-CH₃-6-SCH₃-3-pyridyl | H | " | " | " | " | |
| III-52 | " | CH₃ | " | " | " | " | |
| III-53 | 2-CH₃-6-SOCH₃-3-pyridyl | H | " | " | " | " | |
| III-54 | " | CH₃ | " | " | " | " | |
| III-55 | 2-CH₃-6-SO₂CH₃-3-pyridyl | H | " | " | " | " | [140–1] |
| III-56 | " | CH₃ | " | " | " | " | |
| III-57 | " | H | " | " | CH₃ | " | |
| III-58 | 2-CH₃-6-Cl-3-pyridyl | " | " | " | H | NC₂H₅ | |
| III-59 | 2-CH₃-6-CF₃-3-pyridyl | " | " | " | " | " | |
| III-60 | 2-CH₃-6-SCH₃-3-pyridyl | " | " | " | " | " | |
| III-61 | 2-CH₃-6-SOCH₃-3-pyridyl | " | " | " | " | " | |
| III-62 | 2-CH₃-6-SO₂CH₃-3-pyridyl | H | H | H | H | NC₂H₅ | |
| III-63 | " | CH₃ | " | " | " | " | |
| III-64 | " | H | " | " | CH₃ | " | |
| III-65 | 2-CH₃-6-Cl-3-pyridyl | " | " | " | H | S | |
| III-66 | 2-CH₃-6-SO₂CH₃-3-pyridyl | " | " | " | " | " | |
| III-67 | " | " | " | " | " | " | |

TABLE 3-continued

Structural formula

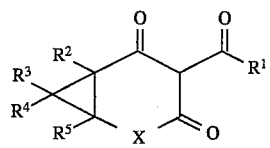

| Compound No. | $R^1$ | $R^2$ | $R^3$ | $R^4$ | $R^5$ | X | Physical constant [ ] m.p. °C. |
|---|---|---|---|---|---|---|---|
| III-68 | 3-Cl-4-pyridyl | " | " | " | " | O | |
| III-69 | 3-NO$_2$-4-pyridyl | " | " | " | " | " | |
| III-70 | 3-CF$_3$-4-pyridyl | " | " | " | " | " | |
| III-71 | 3-Cl-4-pyridyl | " | " | " | " | NH | |
| III-72 | 3-NO$_2$-4-pyridyl | " | " | " | " | " | |
| III-73 | " | CH$_3$ | " | " | " | " | |
| III-74 | 3-CF$_3$-4-pyridyl | H | " | " | " | " | |
| III-75 | " | CH$_3$ | " | " | " | " | |
| III-76 | 3-Cl-4-pyridyl | H | " | " | " | NCH$_3$ | |
| III-77 | 3-NO$_2$-4-pyridyl | " | " | " | " | " | |
| III-78 | 3-NO$_2$-4-pyridyl | CH$_3$ | H | H | H | NCH$_3$ | |
| III-79 | 3-CF$_3$-4-pyridyl | H | " | " | " | " | |
| III-80 | " | CH$_3$ | " | " | " | " | |
| III-81 | 3-Cl-4-pyridyl | H | " | " | " | S | |
| III-82 | 3-NO$_2$-4-pyridyl | " | " | " | " | " | |

TABLE 4

Structural formula

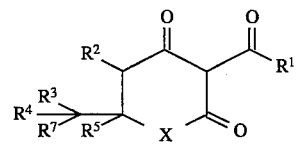

| Compound No. | $R^1$ | $R^2$ | $R^3$ | $R^4$ | $R^5$ | $R^7$ | X | Physical constant [ ] m.p. °C. |
|---|---|---|---|---|---|---|---|---|
| IV-1 | 5-Cl-2-pyridyl | H | H | H | H | OH | O | |
| IV-2 | " | " | " | " | " | OCH$_3$ | " | |
| IV-3 | " | " | " | " | " | OCOCH$_3$ | " | |
| IV-4 | " | " | " | " | " | OSO$_2$CH$_3$ | " | |
| IV-5 | " | " | " | " | CH$_3$ | OH | " | |
| IV-6 | " | " | " | " | " | OCH$_3$ | " | |
| IV-7 | " | " | " | " | " | OCOCH$_3$ | " | |
| IV-8 | " | " | " | " | " | OSO$_2$CH$_3$ | " | |
| IV-9 | 5-CF$_3$-2-pyridyl | " | " | " | H | OH | " | |
| IV-10 | " | " | " | " | " | OCH$_3$ | " | |
| IV-11 | " | " | " | " | " | OCOCH$_3$ | O | |
| IV-12 | " | " | " | " | " | OSO$_2$CH$_3$ | " | |
| IV-13 | " | " | " | " | CH$_3$ | OH | " | |
| IV-14 | " | " | " | " | " | OCH$_3$ | " | |
| IV-15 | " | " | " | " | " | OCOCH$_3$ | " | |
| IV-16 | " | " | " | " | " | OSO$_2$CH$_3$ | " | |
| IV-17 | 5-SCH$_3$-2-pyridyl | " | " | " | H | OH | " | |
| IV-18 | " | " | " | " | " | OCH$_3$ | " | |
| IV-19 | " | " | " | " | " | OCOCH$_3$ | " | |
| IV-20 | " | " | " | " | " | OSO$_2$CH$_3$ | " | |
| IV-21 | " | " | " | " | CH$_3$ | OH | " | |
| IV-22 | " | " | " | " | " | OCH$_3$ | " | |
| IV-23 | " | " | " | " | " | OCOCH$_3$ | " | |
| IV-24 | " | " | " | " | " | OSO$_2$CH$_3$ | " | |
| IV-25 | 5-SO$_2$CH$_3$-2-pyridyl | H | H | H | H | OH | O | |
| IV-26 | " | " | " | " | " | OCH$_3$ | " | |
| IV-27 | " | " | " | " | " | OCOCH$_3$ | " | |
| IV-28 | " | " | " | " | " | OSO$_2$CH$_3$ | " | |
| IV-29 | " | " | " | " | CH$_3$ | OH | " | |
| IV-30 | " | " | " | " | " | OCH$_3$ | " | |
| IV-31 | " | " | " | " | " | OCOCH$_3$ | " | |
| IV-32 | " | " | " | " | " | OSO$_2$CH$_3$ | " | |
| IV-33 | 5-Cl-2-pyridyl | " | " | " | H | OH | NH | |
| IV-34 | " | " | " | " | " | OCH$_3$ | " | |
| IV-35 | " | " | " | " | " | OCOCH$_3$ | " | |

TABLE 4-continued

Structural formula $$R^4\underset{R^7}{\overset{R^3}{-}}R^5-\underset{X}{\overset{R^2}{C}H}-\underset{O}{\overset{O}{C}}-CH-\underset{O}{\overset{O}{C}}-R^1$$

| Compound No. | $R^1$ | $R^2$ | $R^3$ | $R^4$ | $R^5$ | $R^7$ | X | Physical constant [ ] m.p. °C. |
|---|---|---|---|---|---|---|---|---|
| IV-36 | " | " | " | " | " | $OSO_2CH_3$ | " | |
| IV-37 | " | $CH_3$ | " | " | " | OH | " | |
| IV-38 | " | " | " | " | " | $OCH_3$ | " | |
| IV-39 | " | " | " | " | " | $OCOCH_3$ | NH | |
| IV-40 | " | " | " | " | " | $OSO_2CH_3$ | " | |
| IV-41 | 5-$CF_3$-2-pyridyl | H | " | " | " | OH | " | |
| IV-42 | " | " | " | " | " | $OCH_3$ | " | |
| IV-43 | " | " | " | " | " | $OCOCH_3$ | " | |
| IV-44 | " | " | " | " | " | $OSO_2CH_3$ | " | |
| IV-45 | " | $CH_3$ | " | " | " | OH | " | |
| IV-46 | " | " | " | " | " | $OCH_3$ | " | |
| IV-47 | " | " | " | " | " | $OCOCH_3$ | " | |
| IV-48 | " | " | " | " | " | $OSO_2CH_3$ | " | |
| IV-49 | 5-$SCH_3$-2-pyridyl | H | " | " | " | OH | " | |
| IV-50 | " | " | " | " | " | $OCH_3$ | " | |
| IV-51 | " | " | " | " | " | $OCOCH_3$ | " | |
| IV-52 | " | " | " | " | " | $OSO_2CH_3$ | " | |
| IV-53 | " | $CH_3$ | " | " | " | OH | NH | |
| IV-54 | " | " | " | " | " | $OCH_3$ | " | |
| IV-55 | " | " | " | " | " | $OCOCH_3$ | " | |
| IV-56 | " | " | " | " | " | $OSO_2CH_3$ | " | |
| IV-57 | 5-$SO_2CH_3$-2-pyridyl | H | " | " | " | OH | " | |
| IV-58 | " | " | " | " | " | $OCH_3$ | " | |
| IV-59 | " | " | " | " | " | $OCOCH_3$ | " | |
| IV-60 | " | " | " | " | " | $OSO_2CH_3$ | " | |
| IV-61 | " | $CH_3$ | " | " | " | OH | " | |
| IV-62 | " | " | " | " | " | $OCH_3$ | " | |
| IV-63 | " | " | " | " | " | $OCOCH_3$ | " | |
| IV-64 | " | " | " | " | " | $OSO_2CH_3$ | " | |
| IV-65 | 5-Cl-2-pyridyl | H | " | " | " | OH | $NCH_3$ | |
| IV-66 | " | " | " | " | " | $OCH_3$ | " | |
| IV-67 | " | " | " | " | " | $OCOCH_3$ | " | |
| IV-68 | " | " | " | " | " | $OSO_2CH_3$ | " | |
| IV-69 | " | $CH_3$ | " | " | " | OH | " | |
| IV-70 | " | " | " | " | " | $OCH_3$ | " | |
| IV-71 | " | " | " | " | " | $OCOCH_3$ | " | |
| IV-72 | " | " | " | " | " | $OSO_2CH_3$ | " | |
| IV-73 | 5-$CF_3$-2-pyridyl | H | " | " | " | OH | " | |
| IV-74 | " | " | " | " | " | $OCH_3$ | " | |
| IV-75 | " | " | " | " | " | $OCOCH_3$ | " | |
| IV-76 | " | " | " | " | " | $OSO_2CH_3$ | " | |
| IV-77 | " | $CH_3$ | " | " | " | OH | " | |
| IV-78 | " | " | " | " | " | $OCH_3$ | " | |
| IV-79 | " | " | " | " | " | $OCOCH_3$ | " | |
| IV-80 | " | " | " | " | " | $OSO_2CH_3$ | " | |
| IV-81 | " | " | " | " | " | OH | " | |
| IV-82 | " | " | " | " | " | $OCH_3$ | " | |
| IV-83 | " | " | " | " | " | $OCOCH_3$ | " | |
| IV-84 | " | " | " | " | " | $OSO_2CH_3$ | " | |
| IV-85 | " | $CH_3$ | " | " | " | OH | " | |
| IV-86 | " | " | " | " | " | $OCH_3$ | " | |
| IV-87 | " | " | " | " | " | $OCOCH_3$ | " | |
| IV-88 | " | " | " | " | " | $OSO_2CH_3$ | " | |
| IV-89 | 5-$SO_2CH_3$-2-pyridyl | H | " | " | " | OH | " | |
| IV-90 | " | " | " | " | " | $OCH_3$ | " | |
| IV-91 | " | " | " | " | " | $OCOCH_3$ | " | |
| IV-92 | " | " | " | " | " | $OSO_2CH_3$ | " | |
| IV-93 | " | $CH_3$ | " | " | " | OH | " | |
| IV-94 | " | " | " | " | " | $OCH_3$ | " | |
| IV-95 | " | " | " | " | " | $OCOCH_3$ | " | |
| IV-96 | " | " | " | " | " | $OSO_2CH_3$ | " | |
| IV-97 | 5-Cl-2-pyridyl | H | " | " | " | OH | S | |
| IV-98 | " | " | " | " | " | $OCH_3$ | " | |
| IV-99 | " | " | " | " | " | $OCOCH_3$ | " | |
| IV-100 | " | " | " | " | " | $OSO_2CH_3$ | " | |
| IV-101 | 5-$SO_2CH_3$-2-pyridyl | " | " | " | " | OH | " | |
| IV-102 | " | " | " | " | " | $OCH_3$ | " | |

TABLE 4-continued

Structural formula

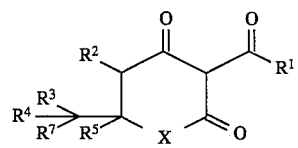

| Compound No. | R¹ | R² | R³ | R⁴ | R⁵ | R⁷ | X | Physical constant [ ] m.p. °C. |
|---|---|---|---|---|---|---|---|---|
| IV-103 | " | " | " | " | " | OCOCH₃ | " | |
| IV-104 | " | " | " | " | " | OSO₂CH₃ | " | |
| IV-105 | 2-CH₃-6-Cl-3-pyridyl | " | " | " | " | OH | O | |
| IV-106 | " | " | " | " | " | OCH₃ | " | |
| IV-107 | " | " | " | " | " | OCOCH₃ | " | |
| IV-108 | " | " | " | " | " | OSO₂CH₃ | " | |
| IV-109 | " | " | " | " | CH₃ | OH | " | |
| IV-110 | " | " | " | " | " | OCH₃ | " | |
| IV-111 | " | " | " | " | " | OCOCH₃ | " | |
| IV-112 | " | " | " | " | " | OSO₂CH₃ | " | |
| IV-113 | 2-CH₃-6-CF₃-3-pyridyl | " | " | " | H | OH | " | |
| IV-114 | " | " | " | " | " | OCH₃ | " | |
| IV-115 | " | " | " | " | " | OCOCH₃ | " | |
| IV-116 | " | " | " | " | " | OSO₂CH₃ | " | |
| IV-117 | " | " | " | " | CH₃ | OH | " | |
| IV-118 | " | " | " | " | " | OCH₃ | " | |
| IV-119 | " | " | " | " | " | OCOCH₃ | " | |
| IV-120 | " | " | " | " | " | OSO₂CH₃ | " | |
| IV-121 | 2-CH₃-6-SCH₃-3-pyridyl | " | " | " | H | OH | " | |
| IV-122 | " | " | " | " | " | OCH₃ | " | |
| IV-123 | " | " | " | " | " | OCOCH₃ | " | |
| IV-124 | " | " | " | " | " | OSO₂CH₃ | " | |
| IV-125 | " | " | " | " | CH₃ | OH | " | |
| IV-126 | " | " | " | " | " | OCH₃ | " | |
| IV-127 | " | " | " | " | " | OCOCH₃ | " | |
| IV-128 | " | " | " | " | " | OSO₂CH₃ | " | |
| IV-129 | 2-CH₃-6-SOCH₃-3-pyridyl | " | " | " | H | OH | " | |
| IV-130 | " | " | " | " | " | OCH₃ | " | |
| IV-131 | " | " | " | " | " | OCOCH₃ | " | |
| IV-132 | " | " | " | " | " | OSO₂CH₃ | " | |
| IV-133 | " | " | " | " | CH₃ | OH | " | |
| IV-134 | " | " | " | " | " | OCH₃ | " | |
| IV-135 | " | " | " | " | " | OCOCH₃ | " | |
| IV-136 | " | " | " | " | " | OSO₂CH₃ | " | |
| IV-137 | " | " | " | " | H | OH | " | |
| IV-138 | " | " | " | " | " | OCH₃ | " | |
| IV-139 | " | " | " | " | " | OCOCH₃ | " | |
| IV-140 | " | " | " | " | " | OSO₂CH₃ | " | |
| IV-141 | " | " | " | " | CH₃ | OH | " | |
| IV-142 | " | " | " | " | " | OCH₃ | " | |
| IV-143 | " | " | " | " | " | OCOCH₃ | " | |
| IV-144 | " | " | " | " | " | OSO₂CH₃ | " | |
| IV-145 | 2-CH₃-6-Cl-3-pyridyl | " | " | " | H | OH | NH | |
| IV-146 | " | " | " | " | " | OCH₃ | " | |
| IV-147 | " | " | " | " | " | OCOCH₃ | " | |
| IV-148 | " | " | " | " | " | OSO₂CH₃ | " | |
| IV-149 | " | CH₃ | " | " | " | OH | " | |
| IV-150 | " | " | " | " | " | OCH₃ | " | |
| IV-151 | " | " | " | " | " | OCOCH₃ | " | |
| IV-152 | " | " | " | " | " | OSO₂CH₃ | " | |
| IV-153 | " | H | " | " | " | OH | NCH₃ | [146–8° C.] |
| IV-154 | " | " | " | " | " | OCH₃ | " | [105–7° C.] |
| IV-155 | " | " | " | " | " | OCOCH₃ | " | |
| IV-156 | " | " | " | " | " | OSO₂CH₃ | " | |
| IV-157 | " | CH₃ | " | " | " | OH | " | |
| IV-158 | " | " | " | " | " | OCH₃ | " | |
| IV-159 | " | " | " | " | " | OCOCH₃ | " | |
| IV-160 | " | " | " | " | " | OSO₂CH₃ | " | |
| IV-161 | " | H | " | " | " | OH | NC₂H₅ | |
| IV-162 | " | " | " | " | " | OCH₃ | " | |
| IV-163 | " | " | " | " | " | OCOCH₃ | " | |
| IV-164 | " | " | " | " | " | OSO₂CH₃ | " | |
| IV-165 | " | " | " | " | " | OH | NH | |
| IV-166 | " | " | " | " | " | OCH₃ | " | |
| IV-167 | " | " | " | " | " | OCOCH₃ | " | |
| IV-168 | " | " | " | " | " | OSO₂CH₃ | " | |
| IV-169 | " | CH₃ | " | " | " | OH | " | |

TABLE 4-continued

Structural formula

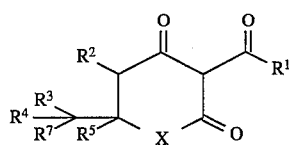

| Compound No. | R¹ | R² | R³ | R⁴ | R⁵ | R⁷ | X | Physical constant [ ] m.p. °C. |
|---|---|---|---|---|---|---|---|---|
| IV-170 | " | " | " | " | " | OCH₃ | " | |
| IV-171 | " | " | " | " | " | OCOCH₃ | " | |
| IV-172 | " | " | " | " | " | OSO₂CH₃ | " | |
| IV-173 | " | H | " | " | " | OH | NCH₃ | |
| IV-174 | " | " | " | " | " | OCH₃ | " | |
| IV-175 | " | " | " | " | " | OCOCH₃ | " | |
| IV-176 | " | " | " | " | " | OSO₂CH₃ | " | |
| IV-177 | " | CH₃ | " | " | " | OH | " | |
| IV-178 | " | " | " | " | " | OCH₃ | " | |
| IV-179 | " | " | " | " | " | OCOCH₃ | " | |
| IV-180 | " | " | " | " | " | OSO₂CH₃ | " | |
| IV-181 | " | H | " | " | " | OH | NC₂H₅ | |
| IV-182 | " | " | " | " | " | OCH₃ | " | |
| IV-183 | " | " | " | " | " | OCOCH₃ | " | |
| IV-184 | " | " | " | " | " | OSO₂CH₃ | " | |
| IV-185 | 2-CH₃-6-SCH₃-3-pyridyl | " | " | " | " | OH | NH | |
| IV-186 | " | " | " | " | " | OCH₃ | " | |
| IV-187 | " | " | " | " | " | OCOCH₃ | " | |
| IV-188 | " | " | " | " | " | OSO₂CH₃ | " | |
| IV-189 | " | CH₃ | " | " | " | OH | " | |
| IV-190 | " | " | " | " | " | OCH₃ | " | |
| IV-191 | " | " | " | " | " | OCOCH₃ | " | |
| IV-192 | " | " | " | " | " | OSO₂CH₃ | " | |
| IV-193 | 2-CH₃-6-SCH₃-3-pyridyl | H | H | H | H | OH | NCH₃ | |
| IV-194 | " | " | " | " | " | OCH₃ | " | |
| IV-195 | " | " | " | " | " | OCOCH₃ | " | |
| IV-196 | " | " | " | " | " | OSO₂CH₃ | " | |
| IV-197 | " | CH₃ | " | " | " | OH | " | |
| IV-198 | " | " | " | " | " | OCH₃ | " | |
| IV-199 | " | " | " | " | " | OCOCH₃ | " | |
| IV-200 | " | " | " | " | " | OSO₂CH₃ | " | |
| IV-201 | " | H | " | " | " | OH | NC₂H₅ | |
| IV-202 | " | " | " | " | " | OCH₃ | " | |
| IV-203 | " | " | " | " | " | OCOCH₃ | " | |
| IV-204 | " | " | " | " | " | OSO₂CH₃ | " | |
| IV-205 | 2-CH₃-6-SOCH₃-3-pyridyl | " | " | " | " | OH | NH | |
| IV-206 | " | " | " | " | " | OCH₃ | " | |
| IV-207 | 2-CH₃-6-SOCH₃-3-pyridyl | H | H | H | H | OCOCH₃ | NH | |
| IV-208 | " | " | " | " | " | OSO₂CH₃ | " | |
| IV-209 | " | CH₃ | " | " | " | OH | " | |
| IV-210 | " | " | " | " | " | OCH₃ | " | |
| IV-211 | " | " | " | " | " | OCOCH₃ | " | |
| IV-212 | " | " | " | " | " | OSO₂CH₃ | " | |
| IV-213 | " | H | " | " | " | OH | NCH₃ | |
| IV-214 | " | " | " | " | " | OCH₃ | " | |
| IV-215 | " | " | " | " | " | OCOCH₃ | " | |
| IV-216 | " | " | " | " | " | OSO₂CH₃ | " | |
| IV-217 | " | CH₃ | " | " | " | OH | " | |
| IV-218 | " | " | " | " | " | OCH₃ | " | |
| IV-219 | " | " | " | " | " | OCOCH₃ | " | |
| IV-220 | " | " | " | " | " | OSO₂CH₃ | " | |
| IV-221 | 2-CH₃-6-SOCH₃-3-pyridyl | H | H | H | H | OH | NC₂H₅ | |
| IV-222 | " | " | " | " | " | OCH₃ | " | |
| IV-223 | " | " | " | " | " | OCOCH₃ | " | |
| IV-224 | " | " | " | " | " | OSO₂CH₃ | " | |
| IV-225 | 2-CH₃-6-SO₂CH₃-3-pyridyl | " | " | " | " | OH | NH | |
| IV-226 | " | " | " | " | " | OCH₃ | " | |
| IV-227 | " | " | " | " | " | OCOCH₃ | " | |
| IV-228 | " | " | " | " | " | OSO₂CH₃ | " | |
| IV-229 | " | CH₃ | " | " | " | OH | " | |
| IV-230 | " | " | " | " | " | OCH₃ | " | |
| IV-231 | " | " | " | " | " | OCOCH₃ | " | |
| IV-232 | " | " | " | " | " | OSO₂CH₃ | " | |
| IV-233 | " | H | " | " | " | OH | NCH₃ | [155–6] |
| IV-234 | " | " | " | " | " | OCH₃ | " | [135–7] |
| IV-235 | 2-CH₃-6-SO₂CH₃-3-pyridyl | H | H | H | H | OCOCH₃ | NCH₃ | |
| IV-236 | " | " | " | " | " | OSO₂CH₃ | " | |

TABLE 4-continued

Structural formula

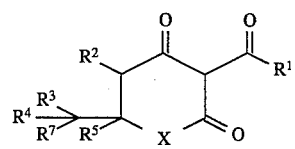

| Compound No. | R¹ | R² | R³ | R⁴ | R⁵ | R⁷ | X | Physical constant [ ] m.p. °C. |
|---|---|---|---|---|---|---|---|---|
| IV-237 | " | CH₃ | " | " | " | OH | " | |
| IV-238 | " | " | " | " | " | OCH₃ | " | |
| IV-239 | " | " | " | " | " | OCOCH₃ | " | |
| IV-240 | " | " | " | " | " | OSO₂CH₃ | " | |
| IV-241 | " | H | " | " | CH₃ | OH | " | |
| IV-242 | " | " | " | " | " | OCH₃ | " | |
| IV-243 | " | " | " | " | " | OCOCH₃ | " | |
| IV-244 | " | " | " | " | " | OSO₂CH₃ | " | |
| IV-245 | " | " | " | " | H | OH | NC₂H₅ | |
| IV-246 | " | " | " | " | " | OCH₃ | " | |
| IV-247 | " | " | " | " | " | OCOCH₃ | " | |
| IV-248 | " | " | " | " | " | OSO₂CH₃ | " | |
| IV-249 | 2-CH₃-6-SO₂CH₃-3-pyridyl | CH₃ | H | H | H | OH | NC₂H₅ | |
| IV-250 | " | " | " | " | " | OCH₃ | " | |
| IV-251 | " | " | " | " | " | OCOCH₃ | " | |
| IV-252 | " | " | " | " | " | OSO₂CH₃ | " | |
| IV-253 | " | H | " | " | CH₃ | OH | " | |
| IV-254 | " | " | " | " | " | OCH₃ | " | |
| IV-255 | " | " | " | " | " | OCOCH₃ | " | |
| IV-256 | " | " | " | " | " | OSO₂CH₃ | " | |
| IV-257 | 2-CH₃-6-Cl-3-pyridyl | " | " | " | H | OH | S | |
| IV-258 | 2-CH₃-6-SO₂CH₃-3-pyridyl | " | " | " | " | OCH₃ | " | |
| IV-259 | 3-Cl-4-pyridyl | " | " | " | " | OH | O | |
| IV-260 | " | " | " | " | " | OCH₃ | " | |
| IV-261 | " | " | " | " | " | OCOCH₃ | " | |
| IV-262 | " | " | " | " | " | OSO₂CH₃ | " | |
| IV-263 | 3-NO₂-4-pyridyl | H | H | H | H | OH | O | |
| IV-264 | " | " | " | " | " | OCH₃ | " | |
| IV-265 | " | " | " | " | " | OCOCH₃ | " | |
| IV-266 | " | " | " | " | " | OSO₂CH₃ | " | |
| IV-267 | 3-CF₃-4-pyridyl | " | " | " | " | OH | " | |
| IV-268 | " | " | " | " | " | OCH₃ | " | |
| IV-269 | " | " | " | " | " | OCOCH₃ | " | |
| IV-270 | " | " | " | " | " | OSO₂CH₃ | " | |
| IV-271 | 3-Cl-4-pyridyl | " | " | " | " | OH | NH | |
| IV-272 | " | " | " | " | " | OCH₃ | " | |
| IV-273 | " | " | " | " | " | OCOCH₃ | " | |
| IV-274 | " | " | " | " | " | OSO₂CH₃ | " | |
| IV-275 | " | " | " | " | " | OH | NCH₃ | |
| IV-276 | " | " | " | " | " | OCH₃ | " | |
| IV-277 | 3-Cl-4-pyridyl | H | H | H | H | OCOCH₃ | NCH₃ | |
| IV-278 | " | " | " | " | " | OSO₂CH₃ | " | |
| IV-279 | 3-NO₂-4-pyridyl | " | " | " | " | OH | NH | |
| IV-280 | " | " | " | " | " | OCH₃ | " | |
| IV-281 | " | " | " | " | " | OCOCH₃ | " | |
| IV-282 | " | " | " | " | " | OSO₂CH₃ | " | |
| IV-283 | " | CH₃ | " | " | " | OH | " | |
| IV-284 | " | " | " | " | " | OCH₃ | " | |
| IV-285 | " | " | " | " | " | OCOCH₃ | " | |
| IV-286 | " | " | " | " | " | OSO₂CH₃ | " | |
| IV-287 | " | H | " | " | " | OH | NCH₃ | |
| IV-288 | " | " | " | " | " | OCH₃ | " | |
| IV-289 | " | " | " | " | " | OCOCH₃ | " | |
| IV-290 | " | " | " | " | " | OSO₂CH₃ | " | |
| IV-291 | 3-NO₂-4-pyridyl | CH₃ | H | H | H | OH | NCH₃ | |
| IV-292 | " | " | " | " | " | OCH₃ | " | |
| IV-293 | " | " | " | " | " | OCOCH₃ | " | |
| IV-294 | " | " | " | " | " | OSO₂CH₃ | " | |
| IV-295 | 3-CF₃-4-pyridyl | H | " | " | " | OH | NH | |
| IV-296 | " | " | " | " | " | OCH₃ | " | |
| IV-297 | " | " | " | " | " | OCOCH₃ | " | |
| IV-298 | " | " | " | " | " | OSO₂CH₃ | " | |
| IV-299 | " | CH₃ | " | " | " | OH | " | |
| IV-300 | " | " | " | " | " | OCH₃ | " | |
| IV-301 | " | " | " | " | " | OCOCH₃ | " | |
| IV-302 | " | " | " | " | " | OSO₂CH₃ | " | |
| IV-303 | " | H | " | " | " | OH | NCH₃ | |

TABLE 4-continued

Structural formula

| Compound No. | R¹ | R² | R³ | R⁴ | R⁵ | R⁷ | X | Physical constant [ ] m.p. °C. |
|---|---|---|---|---|---|---|---|---|
| IV-304 | " | " | " | " | " | OCH$_3$ | " | |
| IV-305 | 3-CF$_3$-4-pyridyl | H | H | H | H | OCOCH$_3$ | NCH$_3$ | |
| IV-306 | " | " | " | " | " | OSO$_2$CH$_3$ | " | |
| IV-307 | 3-NO$_2$-4-pyridyl | CH$_3$ | " | " | " | OH | " | |
| IV-308 | " | " | " | " | " | OCH$_3$ | " | |
| IV-309 | " | " | " | " | " | OCOCH$_3$ | " | |
| IV-310 | " | " | " | " | " | OSO$_2$CH$_3$ | " | |
| IV-311 | 3-Cl-4-pyridyl | H | " | " | " | OH | S | |
| IV-312 | " | " | " | " | " | OCH$_3$ | " | |
| IV-313 | " | " | " | " | " | OCOCH$_3$ | " | |
| IV-314 | " | " | " | " | " | OSO$_2$CH$_3$ | " | |
| IV-315 | 3-NO$_2$-4-pyridyl | " | " | " | " | OH | " | |
| IV-316 | " | " | " | " | " | OCH$_3$ | " | |
| IV-317 | " | " | " | " | " | OCOCH$_3$ | " | |
| IV-318 | " | " | " | " | " | OSO$_2$CH$_3$ | " | |

The compounds of the present invention show high herbicidal activity in either method of soil application or foliar application in upland crop farming condition. When the compounds are applied particularly by foliar application, those show high herbicidal activity against various upland crop weeds such as crabgrass, rice flatsedge, Velvet leaf, and redroot pigweed, and some of those compounds show selectivity on crops such as maize, cereals, soybean, etc.

In the compounds of the present invention, the compounds which have growth regulating action on crops, ornamental plants, fruit trees, etc. are included.

The compounds of the present invention have excellent herbicidal activity on weeds in paddy rice fields such as barnyardgrass, smallflower umbrellaplant, arrowhead, and Japanese bulrush, and the compounds having selectivity on rice are also included thereto.

Furthermore, the compounds of the present invention can be applied for weed control in the fields of fruit trees, turf, railway sides, vacant grounds, etc.

The herbicides according to the present invention comprise 1 or more compounds represented by the general formula [I] described above as their active ingredients and is formulated in the same manner as done for ordinary formulation of agricultural chemicals. More particularly, an adequate amount of the compounds to be used as an active ingredient are generally mixed with carrier to formulate wettable powders, emulsifiable concentrates, granules, water soluble powders, flowables, etc. for practical uses. For the solid carriers, talc, white carbon (silica), bentonite, clay, diatomaceous earth and the like can be exemplified. For the liquid carriers, water, alcohols, benzene, kerosine, mineral oils, cyclohexane, cyclohexanone, dimethylformamide and the like can be exemplified. In these formulations, surface active agents can be added thereto for improving the uniformity and stability thereof, if necessary.

The content of the active ingredients in the formulation of the herbicides of the present invention can be adjusted depending upon the type of the formulation described above, however, those are normally 5 to 70%, preferably 10 to 30% for the wettable powders; 3 to 70%, preferably 5 to 20% for the emulsifiable concentrates; 0.01 to 30%, preferably 0.05 to 10% for the granules.

The wettable powder and the emulsifiable concentrate obtained as described above are applied in a form of either suspension or emulsion after diluting with water to a certain concentration, and the granules is applied in a form as it is by spraying to soil or incorporating with soil at either before or after weed germination. In a case of practical application of the formulations described above, an adequate amount more than 1 g/10 are based on the active ingredient is applied to the objective weeds or soil.

In addition, the compounds of the present invention can be used in a mixture with known fungicides, insecticides, acaricides, herbicides, plant growth regulators, etc. In particular, the mixing with other herbicides can reduce a required dosage for each herbicides. Furthermore, such mixing of herbicides may give not only less labour requirement but also higher herbicidal activity if a synergistic action is obtained with such combination. Naturally, the combination with plural known herbicides is also allowable. The herbicides suitable to mix with the compounds of the present invention include carbamate or thiocarbamate herbicides, such as benthiocarb, molinate, and MY-93 [S-(2,2-dimethylbenzyl)-1-piperidinecarbothioate]; acid amine herbicides, such as butachlor, pretilachlor, and mefenacet; diphenylether herbicides, such as chlomethoxynil and bifenox; triazine herbicides, such as atrazine and cycnazine; sulfonylurea herbicides, such as chlorsulfuron and sulfometuronmethyl; phenoxylalkane carboxylate herbicides, such as MCP and MCPB; phenoxypropionic acid herbicides, such as dichlofop-methyl; pyridyloxyphenoxypropionic acid herbicides, such as fluazifop-butyl; benzoylaminopropionic acid herbicides, such as benzoylprop-ethyl and flamprop-ethyl; and others such as piperophos, dymron, bentazon, difenzoquat, naproanilide, HW-52 (4-ethoxymethoxybenz-2,3-dichloroanilide), KNW-242 [1-(3-methylphenyl)-5-phenyl-1H- 1,2,4-triazole-3-carboxamide], quinclorac (3,7-dichloro-8-quinolinecarboxylic acid); and cyclohexanedione herbicides such as sethoxydim and alloxydim-sodium.

The addition of vegetable oils or oil concentrate to the above mixture is also allowable.

Now, the examples for the formulation prepared for the compounds of the present invention are described below, however, active ingredients, additives, and a portion of addition applicable to the formulations shall not be limited to the ones indicated in the examples, and it is allowable to modify in a wide range.

EXAMPLE 8

A Wettable Powder

| | |
|---|---|
| A compound of this invention | 20 Parts |
| White carbon | 20 Parts |
| Diatomaceous earth | 52 Parts |
| Sodium alkylsulfate | 8 Parts |

All the elements above are homogeneously mixed and micronized to obtain a wettable powder containing 20% active ingredient.

EXAMPLE 9

An Emulsifiable Concentrate

| | |
|---|---|
| A compound of this invention | 20 Parts |
| Xylene | 55 Parts |
| Dimethylformamide | 15 Parts |
| Polyoxyethylenephenylether | 10 Parts |

All the elements above are mixed and dissolved to obtain an emulsifiable concentrate containing 20% active ingredient.

EXAMPLE 10

A Granules

| | |
|---|---|
| A compound of this invention | 5 Parts |
| Talc | 40 Parts |
| Clay | 38 Parts |
| Bentonite | 10 Parts |
| Sodium alkylsulfate | 7 Parts |

All the elements above are homogeneously mixed and micronized, then granulated to granules having a diameter of from 0.5 to 1.0 mm to obtain the granules containing 5% active ingredient.

INDUSTRIAL APPLICATION OF THE INVENTION

Now, test examples on the herbicidal activity of a compound of the present invention are shown below.

Test Example 1

Post-emergence treatment

A pot having a surface area of 200 cm$^2$ was filled with soil, then the respective seeds of crabgrass, giant foxtail, rice flatsedge, and velvet leaf were planted at upper layer of the soil, lightly covered with soil and grown in a greenhouse. When the weeds grew to 5 to 10 cm in height, the emulsion of the emulsifiable concentrate of each test compound adjusted to a concentration of 1,000 ppm by diluting with water were sprayed at a volume 100 liter/10 are (equivalent to 100 g a.i./10 are) to the foliage with small volume sprayer. After 3 weeks, the herbicidal activity of each compound was assessed in accordance with the criteria as shown below. The results shown in Table 5.

| Criteria for the assessment | |
|---|---|
| % of Weeds Killed | Index of Herbicidal Activity |
| 0% | 0 |
| 20–29% | 2 |
| 40–49% | 4 |
| 60–69% | 6 |
| 80–89% | 8 |
| 100% | 10 |

The values of 1, 3, 5, 7 or 9 indicates the intermediate activities of between 0 and 2, 2 and 4, 4 and 6, 6 and 8, or 8 and 10, respectively.

Weeds killed (%)=[(Fresh weight of foliage of the weed untreated−Fresh weight of foliage of the weed in treated)÷Fresh weight of foliage of the weed untreated]×100

TABLE 5

| | | Index of Herbicidal Activity | | | | |
|---|---|---|---|---|---|---|
| Compound No. | Dosage g/10a | Crabgrass | Giant foxtail | Velvet leaf | Redroot pigweed | Rice flatsedge |
| I-2 | 100 | 10 | 10 | 10 | 10 | 10 |
| I-3 | " | " | " | " | " | " |
| I-4 | " | " | " | " | " | " |
| I-5 | " | " | " | " | " | " |
| I-12 | " | " | " | " | " | " |
| I-14 | " | " | " | " | " | " |
| I-16 | " | " | " | " | " | " |
| I-21 | " | " | " | " | " | " |
| I-26 | " | " | " | " | " | " |
| I-33 | " | " | " | " | " | " |
| I-65 | " | " | " | " | " | " |
| I-68 | " | " | " | " | " | " |
| I-71 | " | " | " | " | " | " |
| I-77 | " | " | " | " | " | " |
| I-105 | " | " | " | " | " | " |
| I-148 | " | " | " | " | " | " |

TABLE 5-continued

| Compound No. | Dosage g/10a | Crabgrass | Giant foxtail | Velvet leaf | Redroot pigweed | Rice flatsedge |
|---|---|---|---|---|---|---|
| II-1 | " | " | " | " | " | " |
| II-7 | " | " | " | " | " | " |
| II-33 | " | " | " | " | " | " |
| II-34 | " | " | " | " | " | " |
| II-46 | " | " | " | " | " | " |
| II-63 | " | " | " | " | " | " |
| II-64 | 100 | 10 | 10 | 10 | 10 | 10 |
| II-72 | " | " | " | " | " | " |
| II-83 | " | " | " | " | " | " |
| II-84 | " | " | " | " | " | " |
| II-108 | " | " | " | " | " | " |
| II-110 | " | " | " | " | " | " |
| II-138 | " | " | " | " | " | " |
| II-139 | " | " | " | " | " | " |
| II-199 | " | " | " | " | " | " |
| II-239 | " | " | " | " | " | " |
| II-266 | " | " | " | " | " | " |
| II-267 | " | " | " | " | " | " |
| II-281 | " | " | " | " | " | " |
| II-283 | " | " | " | " | " | " |
| II-296 | " | " | " | " | " | " |
| II-297 | " | " | " | " | " | " |
| II-326 | " | " | " | " | " | " |
| II-336 | " | " | " | " | " | " |
| II-356 | " | " | " | " | " | " |
| II-376 | " | " | " | " | " | " |
| II-419 | " | " | " | " | " | " |
| II-420 | " | " | " | " | " | " |
| II-421 | 100 | 10 | 10 | 10 | 10 | 10 |
| II-424 | " | " | " | " | " | " |
| II-432 | " | " | " | " | " | " |
| II-444 | " | " | " | " | " | " |
| II-635 | " | " | " | " | " | " |
| II-636 | " | " | " | " | " | " |
| II-720 | " | " | " | " | " | " |
| III-47 | " | " | " | " | " | " |
| III-55 | " | " | " | " | " | " |
| IV-153 | " | " | " | " | " | " |
| IV-154 | " | " | " | " | " | " |
| IV-233 | " | " | " | " | " | " |
| IV-234 | " | " | " | " | " | " |

Test Example 2

Pre-emergence treatment

Seeds of crabgrass, giant foxtail, velvet leaf, redroot pigweed and rice flatsedge were planted in a plastic pot (250cm$^2$ surface) containing upland field soil, then covered with soil in a thickness of 0.5 cm. On next day, the dilution of the wettable powder described in the Example 8 was uniformly sprayed over the surface of the soil so as to apply the active ingredient at the rate of 100 g/10 are. After 20 days, the assessment on the herbicidal activities of each compound was conducted in accordance with the criteria described in the Test Example 1. The results were shown in Table 6.

татьBLE 6

| Compound No. | Dosage g/10a | Crabgrass | Giant foxtail | Velvet leaf | Redroot pigweed | Rice flatsedge |
|---|---|---|---|---|---|---|
| I-2 | 100 | 10 | 10 | 10 | 10 | 10 |
| I-3 | " | " | " | " | " | " |
| I-4 | " | " | " | " | " | " |
| I-5 | " | " | " | " | " | " |
| I-21 | " | " | " | " | " | " |
| I-26 | " | " | " | " | " | " |
| I-105 | " | " | " | " | " | " |

TABLE 6-continued

| | | Index of Herbicidal Activity | | | | |
|---|---|---|---|---|---|---|
| Compound No. | Dosage g/10a | Crabgrass | Giant foxtail | Velvet leaf | Redroot pigweed | Rice flatsedge |
| I-148 | " | " | " | " | " | " |
| II-72 | " | " | " | " | " | " |
| II-83 | " | " | " | " | " | " |
| II-84 | " | " | " | " | " | " |
| II-139 | " | " | " | " | " | " |
| II-199 | " | " | " | " | " | " |
| II-239 | " | " | " | " | " | " |
| II-266 | " | " | " | " | " | " |
| II-336 | " | " | " | " | " | " |
| II-419 | " | " | " | " | " | " |
| II-720 | " | " | " | " | " | " |

What we claim is:

1. A heterocyclic cyclohexanedione derivative represented by the formula [I]:

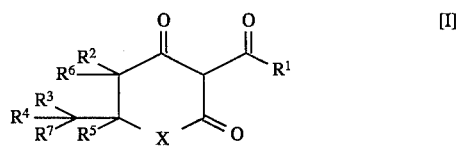

wherein $R^1$ is optionally substituted lower alkyl, optionally substituted cycloalkyl, optionally substituted phenyl or optionally substituted pyridyl ring; $R^2$, $R^3$, $R^4$ and $R^5$ may be the same or different from one another and each independently represents hydrogen, or lower alkyl; $R^6$ is hydrogen; $R^7$ is $OR^8$ wherein $R^8$ is hydrogen, lower alkyl, aralkyl, lower acyl, alkylsulfonyl or arylsulfonyl; or $R^6$ and $R^7$ are combined together to represent a single bond; X is N—$R^9$ wherein $R^9$ is hydrogen, lower alkyl, optionally substituted aralkyl, optionally substituted cycloalkyl or optionally substituted phenyl; and a herbicidally acceptable salt thereof.

2. A herbicidal composition comprising: an effective amount of a compound of the formula [I]

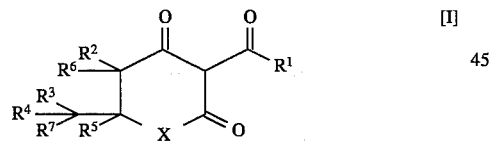

wherein $R^1$ is optionally substituted lower alkyl, optionally substituted cycloalkyl, optionally substituted phenyl or optionally substituted pyridyl ring; $R^2$, $R^3$, $R^4$ and $R^5$ may be the same or different from one another and each independently represents hydrogen, or lower alkyl; $R^6$ is hydrogen; $R^7$ is $OR^8$ wherein $R^8$ is hydrogen, lower alkyl, aralkyl, lower acyl, alkylsulfonyl or arylsulfonyl; or $R^6$ and $R^7$ are combined together to represent a single bond; X is N—$R^9$ wherein $R^9$ is hydrogen, lower alkyl, optionally substituted aralkyl, optionally substituted cycloalkyl or optionally substituted phenyl; and a herbicidally acceptable salt thereof in admixture with a herbicidally inert carrier selected from the group consisting of talc, silica, bentonite clay, diatomaceous earth, water, alcohols, benzene, kerosene, mineral oils, cyclohexane, cyclohexanone, dimethylformamide and mixtures thereof.

3. A method of pre-emergence herbicidal control comprising:

applying a herbicidally effective amount of a compound of the formula [I].

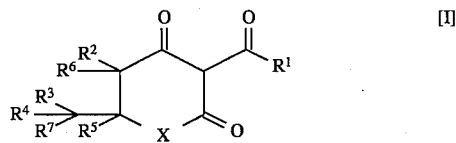

wherein $R^1$ is optionally substituted lower alkyl, optionally substituted cycloalkyl, optionally substituted phenyl or optionally substituted pyridyl ring; $R^2$, $R^3$, $R^4$ and $R^5$ may be the same or different from one another and each independently represents hydrogen, or lower alkyl; $R^6$ is hydrogen; $R^7$ is $OR^8$ wherein $R^8$ is hydrogen, lower alkyl, aralkyl, lower acyl, alkylsulfonyl or arylsulfonyl; or $R^6$ and $R^7$ are combined together to represent a single bond; X is N—$R^9$ wherein $R^9$ is hydrogen, lower alkyl, optionally substituted aralkyl, optionally substituted cycloalkyl or optionally substituted phenyl; and a herbicidally acceptable salt thereof to a pre-emergent habitat selected from the group consisting of crops, ornamental plants, fruit trees, rice fields, turf, railway sides and vacant grounds wherein said herbicidally effective amount of said compound of the formula [I] is sufficient to inhibit the emergence of crabgrass, rice flatsedge, velvet leaf, redroot pigweed, barnyardgrass, smallflower umbrellaplant, arrowhead, giant foxtail and Japanese bulrush in said habitat.

4. A method of post-emergence herbicidal control comprising:

applying a herbicidally effective amount of a compound of the formula [I].

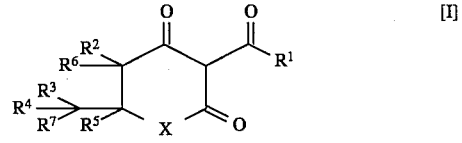

wherein $R^1$ is optionally substituted lower alkyl, optionally substituted cycloalkyl, optionally substituted phenyl or optionally substituted pyridyl ring; $R^2$, $R^3$, $R^4$ and $R^5$ may be the same or different from one another and each independently represents hydrogen, or lower alkyl; $R^6$ is hydrogen; $R^7$ is $OR^8$ wherein $R^8$ is hydrogen, lower alkyl, aralkyl, lower acyl, alkylsulfonyl or arylsulfonyl; or $R^6$ and $R^7$ are combined together to represent a single bond; X is N—$R^9$ wherein $R^9$ is hydrogen, lower alkyl, optionally substituted aralkyl, optionally substituted cycloalkyl or optionally substituted phenyl; and a herbicidally acceptable salt thereof to a post-emergent habitat selected from the group consisting of crops, ornamental plants, fruit trees, rice fields, turf, railway sides and vacant grounds wherein said herbicidally effective amount of said compound of the formula [I] is sufficient to eradicate emergent crabgrass, rice flatsedge, velvet leaf, redroot pigweed, barnyardgrass, smallflower umbrellaplant, arrowhead, giant foxtail and Japanese bulrush in said habitat.

* * * * *